United States Patent
Tsai et al.

(10) Patent No.: US 11,612,624 B2
(45) Date of Patent: Mar. 28, 2023

(54) METHOD FOR PROTECTING A SUBJECT FOR EXERCISE

(71) Applicant: BENED BIOMEDICAL CO., LTD., Taipei (TW)

(72) Inventors: Ying-Chieh Tsai, Taipei (TW); Kuo-Wei Tseng, Taipei (TW); Chih-Chieh Hsu, Taipei (TW); Chien-Chen Wu, Taipei (TW)

(73) Assignee: BENED BIOMEDICAL CO., LTD., Taipei (TW)

( * ) Notice: Subject to any disclaimer, the term of this patent is extended or adjusted under 35 U.S.C. 154(b) by 5 days.

(21) Appl. No.: 17/285,983

(22) PCT Filed: Jan. 22, 2020

(86) PCT No.: PCT/CN2020/073752
§ 371 (c)(1),
(2) Date: Apr. 16, 2021

(87) PCT Pub. No.: WO2020/156417
PCT Pub. Date: Aug. 6, 2020

(65) Prior Publication Data
US 2021/0338750 A1    Nov. 4, 2021

Related U.S. Application Data

(60) Provisional application No. 62/797,720, filed on Jan. 28, 2019.

(51) Int. Cl.
*A61K 35/747* (2015.01)
*A61P 21/00* (2006.01)

(52) U.S. Cl.
CPC ............ *A61K 35/747* (2013.01); *A61P 21/00* (2018.01)

(58) Field of Classification Search
None
See application file for complete search history.

(56) References Cited

FOREIGN PATENT DOCUMENTS

| | | |
|---|---|---|
| CN | 105002109 A | 9/2018 |
| TW | 201811346 A | 4/2018 |
| WO | 2018/014225 A1 | 1/2018 |

OTHER PUBLICATIONS

Liu et al (Brain Research 1631:1-12, 2016).*
International search report for PCT/CN2020/073752 dated Apr. 24, 2020.
Written Opinion for PCT/CN2020/073752 dated Apr. 24, 2020.

* cited by examiner

*Primary Examiner* — Brian Gangle
(74) *Attorney, Agent, or Firm* — Sughrue Mion, PLLC

(57) ABSTRACT

This disclosure provides a method of protecting a subject for exercise that prevents an exercise-related harmful effect and reducing exercise fatigue in the subject to thereby enhance physical performance and promote anti-fatigue and anti-inflammatory effects in the subject.

14 Claims, 25 Drawing Sheets

METHOD FOR PROTECTING A SUBJECT FOR EXERCISE

BACKGROUND

1. Technical Field

This disclosure relates to methods of protecting a subject for exercise, e.g., preventing exercise-related harmful effects and reducing exercise fatigue in the subject to thereby enhance physical performance and increase anti-fatigue and anti-inflammatory effects in the subject.

2. Description of Related Art

Lactic acid bacteria (hereinafter, referred to as LAB) have been recognized as alternatives of prevention or treatment for gut health because of their capability in regulating host's gut microbiota. In recent years, LAB has been found to have several beneficial effects to the health of a host and is able to act as therapeutic means when administered in adequate amounts, including altering host's mental and physical responses for psychological stress, ameliorating allergic responses, preventing or treating functional gastrointestinal disorder such as constipation.

During exercise, muscle damages are often induced. The damages can arise from the increase in exercise-related stress, such as mechanical and inflammatory stress, and affect the performance of the subject. Even in the situations where the muscle damage is minimum, there is always muscle fatigue, or soreness, that results from the abrupt changes in metabolism taking place locally in the muscles. Furthermore, extended and intensive exercises can lead to other unfavorable effects that are not only limited to the muscles but systematic, such as white blood cell activation, inflammation, reactive oxygen species (ROS) production, as well as kidney injury.

It is thus desirable to provide for an efficient method that can reduce or prevent exercise-related muscle damages or fatigue, and protect the subject from other related unfavorable effects, thereby enhancing exercise performance.

SUMMARY

In this disclosure, a lactic acid bacterium strain has been identified to be effective in protecting a subject for exercise, thereby enhancing exercise performance in the subject with an anti-fatigue and an anti-inflammatory effect. The lactic acid bacterium provided in this disclosure is *Lactobacillus plantarum* subsp. *plantarum* PS128 (hereinafter referred to as PS128) that is useful for protecting a subject and enhancing physical performance in the subject. The disclosure also provides a method comprising administering a composition comprising an effective amount of *Lactobacillus plantarum* subsp. *plantarum* PS128 to the subject. The method of this disclosure not only provides a protection effect on reducing inflammation and kidney injuries, but also enhances physical performance that includes increasing physical strength, capacity or endurance, and reduces exercise fatigue or muscle damage.

In one embodiment of this disclosure, a method for protecting a subject and enhancing physical performance in a subject in need thereof is also provided. In accordance with the disclosure, the method comprises administering a composition comprising an effective amount of *Lactobacillus plantarum* subsp. *plantarum* PS128, which is deposited under DSMZ Accession No. DSM 28632, and a carrier thereof. In one embodiment of the disclosure, the composition is orally administrated to the subject in need thereof.

In one embodiment, the effective amount of PS128 administered to the subject is at least $1\times10^9$ CFU. In other embodiments, the effective amount of PS128 is at least $1\times10^9$ CFU, at least $1\times10^{10}$ CFU or at least $1\times10^{11}$ CFU, including $1\times10^9$ CFU, $2\times10^9$ CFU, $3\times10^9$ CFU, $4\times10^9$ CFU, $5\times10^9$ CFU, $6\times10^9$ CFU, $7\times10^9$ CFU, $8\times10^9$ CFU, $9\times10^9$ CFU, $1\times10^{10}$ CFU, $2\times10^{10}$ CFU, $3\times10^{10}$ CFU, $4\times10^{10}$ CFU, $5\times10^{10}$ CFU, $6\times10^{10}$ CFU, $7\times10^{10}$ CFU, $8\times10^{10}$ CFU, $9\times10^{10}$ CFU, $1\times10^{11}$ CFU, $2\times10^{11}$ CFU, $3\times10^{11}$ CFU, $4\times10^{11}$ CFU, $5\times10^{11}$ CFU, $6\times10^{11}$ CFU, $7\times10^{11}$ CFU, $8\times10^{11}$ CFU, and $9\times10^{11}$ CFU, but not limited thereto.

BRIEF DESCRIPTION OF THE DRAWINGS

FIG. 3A shows the creatine kinase level, FIG. 3B shows the myoglobin level, and FIG. 3C shows the lactate dehydrogenase (LDH) level, in placebo and PS128 groups at different time points, respectively. The data are presented as mean±SEM. *$p<0.05$ and **$p<0.01$, comparison made between groups; #$p<0.05$, ##$p<0.01$ and ###$p<0.001$, comparison made within groups.

FIG. 4A shows the TNF-α level, FIG. 4B shows the IFN-γ level, FIG. 4C shows the IL-6 level, and FIG. 4D shows the IL-8 level in the placebo and PS128 groups, respectively. The data are presented as mean±SEM. *$p<0.05$, comparison made between groups; #$p<0.05$, comparison made within groups.

FIG. 5A shows the complement component 5a (C5a) level, FIG. 5B shows the myeloperoxidase (MPO) level, FIG. 5C shows the IL-10 level, and FIG. 5D shows the thioredoxin level in the placebo and PS128 groups, respectively. The data are presented as mean±SEM. *$p<0.05$, comparison made between groups; #$p<0.05$, comparison made within groups.

FIG. 7A shows the peak anaerobic power, FIG. 7B shows the mean anaerobic power, FIG. 7C shows the fatigue index and FIG. 7D shows the exhaustive time in the placebo and PS128 groups, respectively. The data are presented as mean±SEM. *p<0.05, comparison made between groups; #p<0.05, comparison made within groups.

FIG. 8A shows the countermovement jump height, and FIG. 8B shows the countermovement jump power in the placebo and PS128 groups, respectively. The data are presented as mean±SEM. *p<0.05, comparison made between groups; #p<0.05, compared to T0 within groups.

FIG. 9A shows the knee extensor peak torque, FIG. 9B shows the knee extensor average torque, FIG. 9C shows the knee flexor peak torque and FIG. 9D shows the knee flexor average torque in the placebo and PS128 groups, respectively. The data are presented as mean±SEM. *p<0.05, comparison made between groups; #p<0.05, compared to T0 within groups.

DETAILED DESCRIPTION OF THE EMBODIMENTS

As used herein and in the appended claims, the singular forms "a," "an," and "the" include plural references unless the content clearly dictates otherwise.

As used herein the term "fatigue" refers to skeletal muscle fatigue and/or weakness. Muscle fatigue can be due to strenuous or repeated physical activity or exercise that has symptoms of fatigue, or affects myofibers and/or muscle function. Muscle fatigue is defined as the failure of exercise performance. This can be assessed on an exercise stress test and quantified as the time it takes to fail at the given task (e.g. walking, jogging or running on a treadmill). Failure at the task is defined as termination of the exercise due to inability to continue. This is defined as muscle fatigue.

As used herein, "reducing exercise fatigue" refers to lowering of biochemical indices related to muscle fatigue, such as ammonia and branched chain amino acid in the serum.

As used herein, "preventing muscle damage" refers to inhibiting an increase in the blood concentration of muscle damage indicators such as serum myoglobin, lactate dehydrogenase (LDH) or creatine kinase (CK) following exercise. Indicators such as CPK (creatine phosphokinase) are enzymes contained in muscle cells that are released into the blood when muscle damage has occurred, after which the blood concentrations thereof decrease accompanying recovery. Thus, measurement of these muscle damage indicators such as CK can be used as an indicator of muscle damage.

The following examples are used for illustrating the disclosure. A person skilled in the art can easily conceive the other advantages and effects of the disclosure from these examples. The disclosure can also be implemented by various modifications and changes that do not depart from the spirit of the disclosure. It is understood that the examples provided below are only exemplary of the disclosure and should not be taken as a limit to the scope of the disclosure.

EXAMPLES

Example 1: Blood and Urine Sample Analysis Indicates Protecting, Anti-Fatigue and Damage-Reducing Effects of PS128

PS128 was prepared by inoculating in a culture medium, culturing at 37° C. for 18 hours and harvesting by centrifugation. PS128 was embedded and lyophilized with protective agents and excipients to a final concentration of $1\times10^{11}$ colony formation unit (CFU) per gram powder. The lyophilized PS128 powder was encapsulated as capsules. Each capsule included 300 mg of lyophilized bacterial powder, which is equivalent to $3\times10^{10}$ CFU, and 100 mg excipient of microcrystalline cellulose. Placebo capsules were filled with 400 mg excipient of microcrystalline cellulose.

Figure 1:
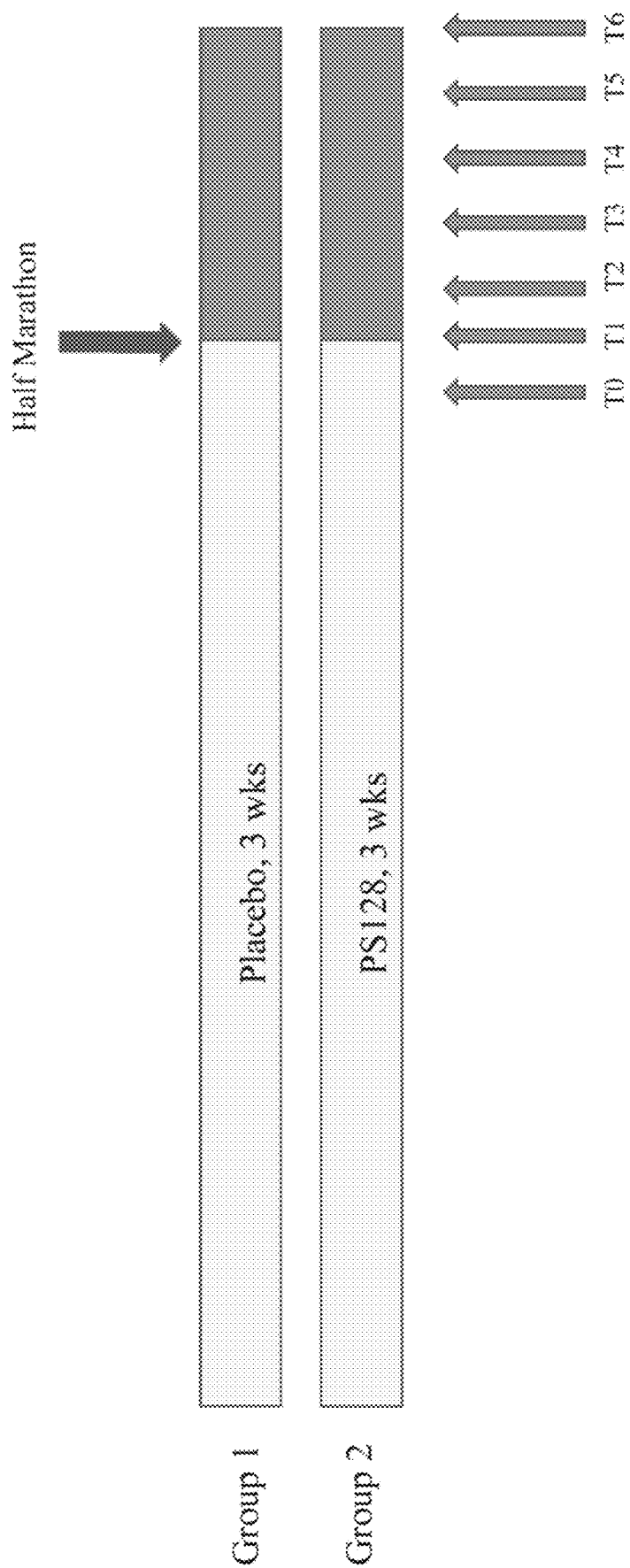
FIG. 1 is an illustrative scheme for subjects divided into placebo (n=4) and PS128 (n=4) groups. The subjects were required to take the capsules two times per day for a total period of three weeks (wks) before undertaking a half marathon as an exercise. Blood and urine samples were obtained from the subjects at seven different time points (T0 to T6), which are at T0: 24 hours (h) before exercise (half marathon); T1: immediately after exercise; T2: 3 h after exercise; T3: 24 h after exercise; T4: 48 h after exercise; T5: 72 h after exercise; and T6: 96 h after exercise.

The subjects recruited in this study were divided into placebo (n=4) and PS128 (n=4) groups, and were required to take the capsules two times (one at a time) per day for a total period of three weeks before undertaking a half marathon. The recruited subjects were prohibited from consuming other probiotics to avoid unnecessary interference during the test period. As shown in Table 1 below and FIG. 1, blood and urine samples were obtained from the recruited subjects at seven different time points (T0 to T6), which are at T0: 24 hours before exercise (pre-test, −24 h); T1: immediately after exercise (0 h); T2: 3 h after exercise (+3 h); T3: 24 h after exercise (+24 h); T4: 48 h after exercise (+48 h); T5: 72 h after exercise (+72 h); and T6: 96 h after exercise (+96 h). For each blood and urine sample obtained, biochemical indices representing muscle fatigue, muscle damage, inflammation, renal function and oxidation stress were analyzed.

TABLE 1

Samples and data collection at different time points

| Data and sample collections | T0 −24 h | T1 0 h | T2 +3 h | T3 +24 h | T4 +48 h | T5 +72 h | T6 +96 h |
|---|---|---|---|---|---|---|---|
| Blood/urine | v | v | v | v | v | v | v |
| VO$_2$ max$^1$ with Bruce protocol* | v | — | — | v | — | — | v |
| Anaerobic power with Wingate protocol** | v | — | v | v | v | v | v |
| EMG MF$^2$ of quadriceps & hamstring | v | v | v | v | v | v | v |
| MVIC$^3$ of quadriceps & hamstring | v | v | v | v | v | v | v |
| Body composition by DEXA$^4$ | v | — | — | v | — | — | v |
| Countermovement jump | v | v | v | v | v | v | v |

Figure 2A:
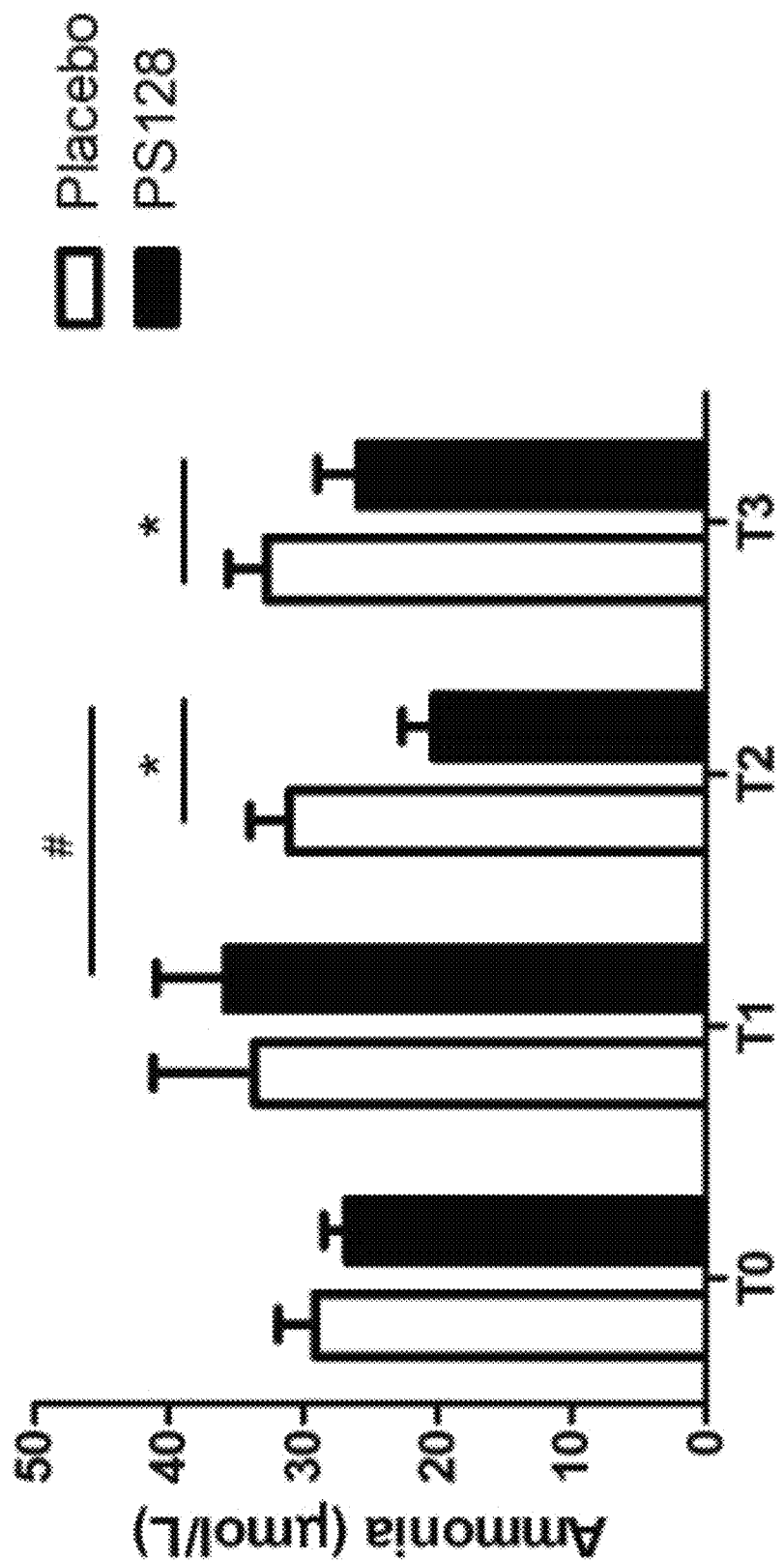
FIGS. 2A and 2B show the levels of biochemical indices, the ammonia levels (FIG. 2A) and the branched chain amino acid levels (FIG. 2B), related to muscle fatigue in placebo and PS128 groups at different time points. The data are presented as mean±SEM. *$p<0.05$, comparison made between groups; #$p<0.05$, comparison made within groups.
Figure 2B:
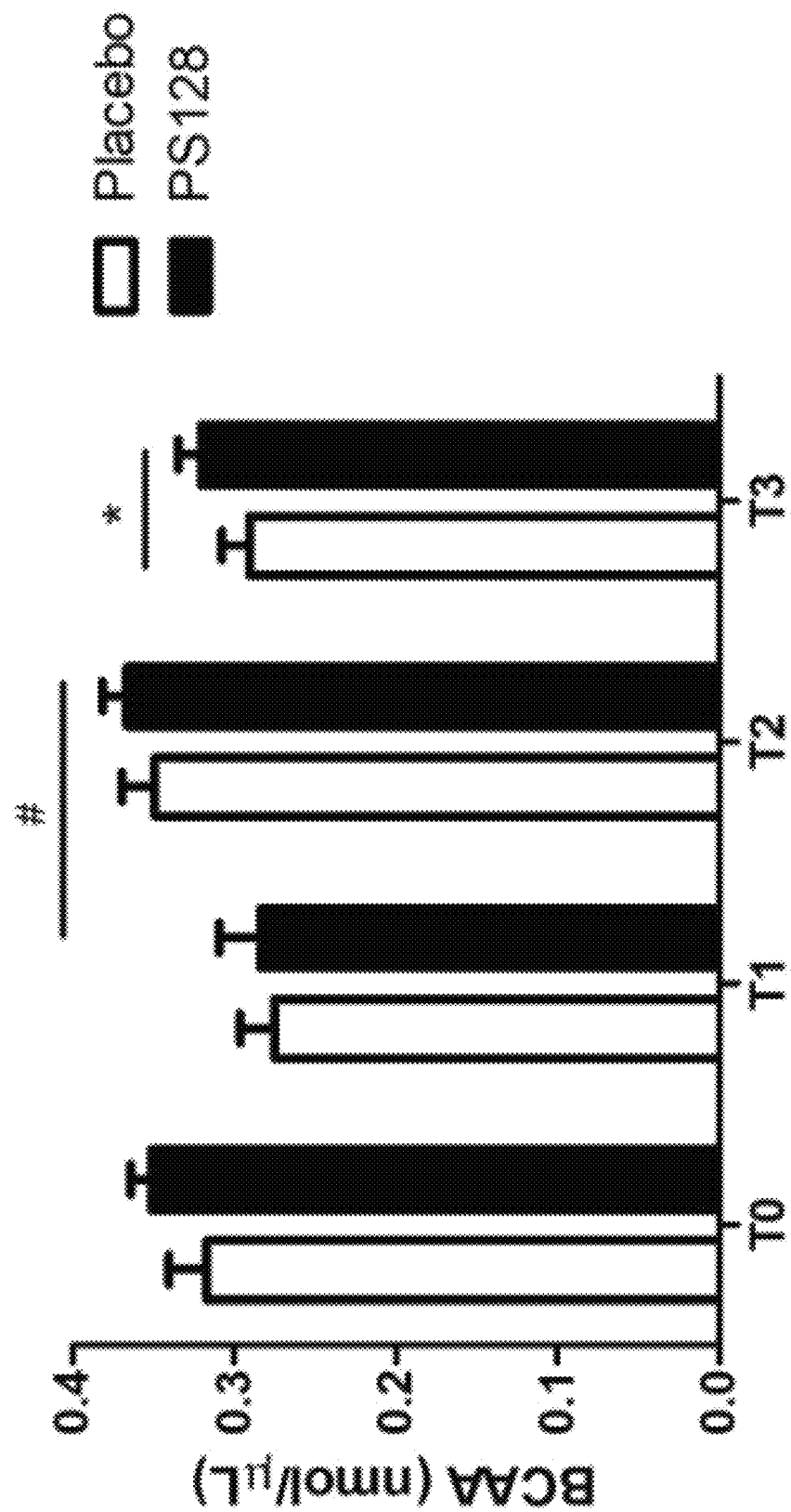

*Nutrition 2018 September; 53: 34-37.
**Biomed. Res. Int. 2014; 2014: 329328.
$^1$VO$_2$ max: the maximum rate of oxygen consumption
$^2$EMG MF: the median frequency of electromyography
$^3$MVIC: maximum voluntary isometric contraction
$^4$DEXA: dual-energy x-ray absorptiometry As shown in FIGS. 2A and 2B, the biochemical indices such as ammonia (FIG. 2A) and branched chain amino acids (BCAAs) (FIG. 2B) related to muscle fatigue showed that there is less fatigue (i.e., lower ammonia levels and higher BCAA levels) observed in the PS128 group as compared to those of the placebo group. It thus demonstrated that BCAAs, such as leucine, isoleucine, and valine, are modulated by PS128. In addition, other amino acids, like threonine, glutamine, and histidine, are also modulated by PS128. Also observed was a lowered level of lactate in the subjects of the PS128 group.

Figure 3A:
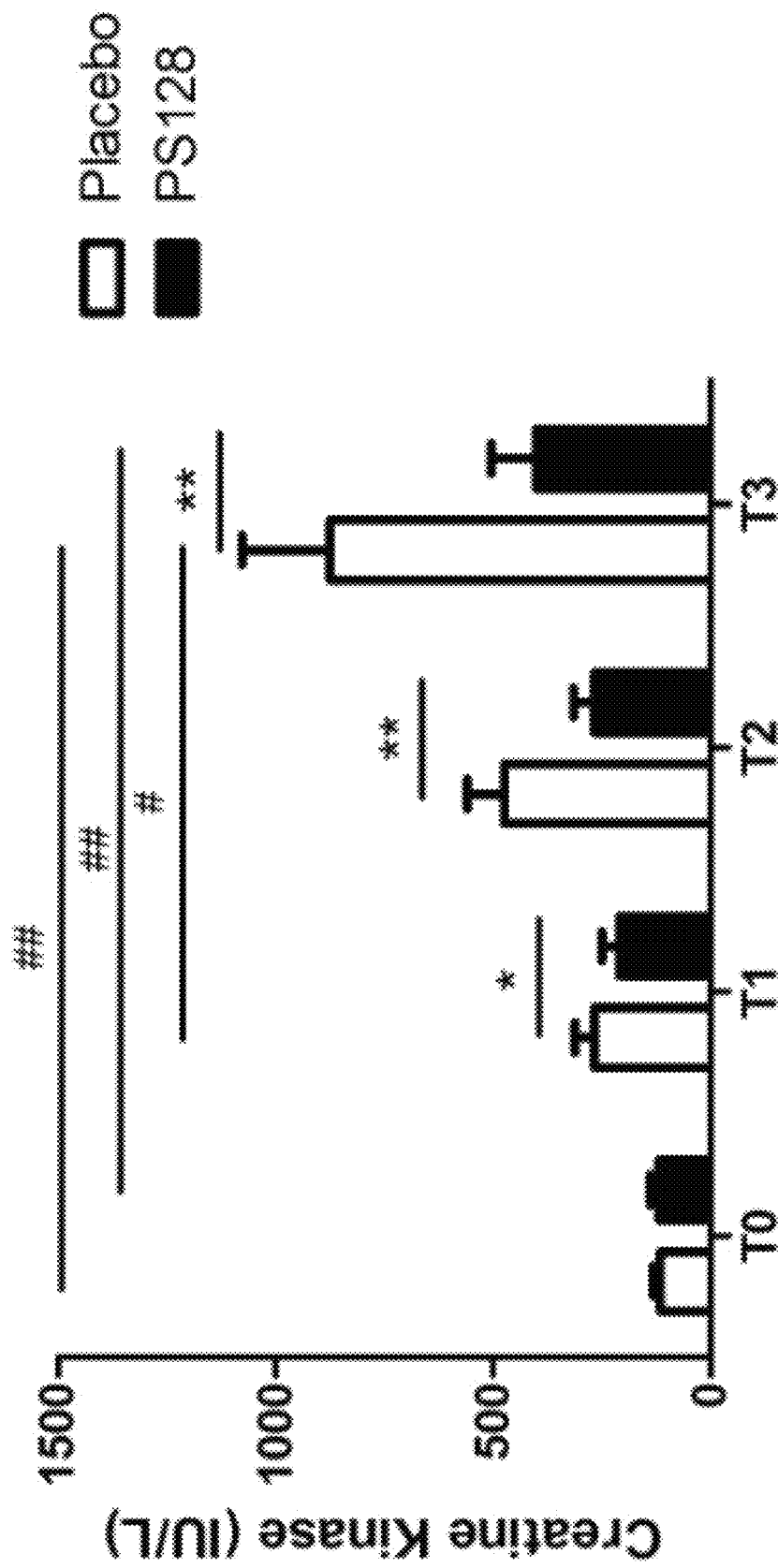
FIGS. 3A to 3C show the levels of biochemical indices related to muscle damage at different time points.
Figure 3B:
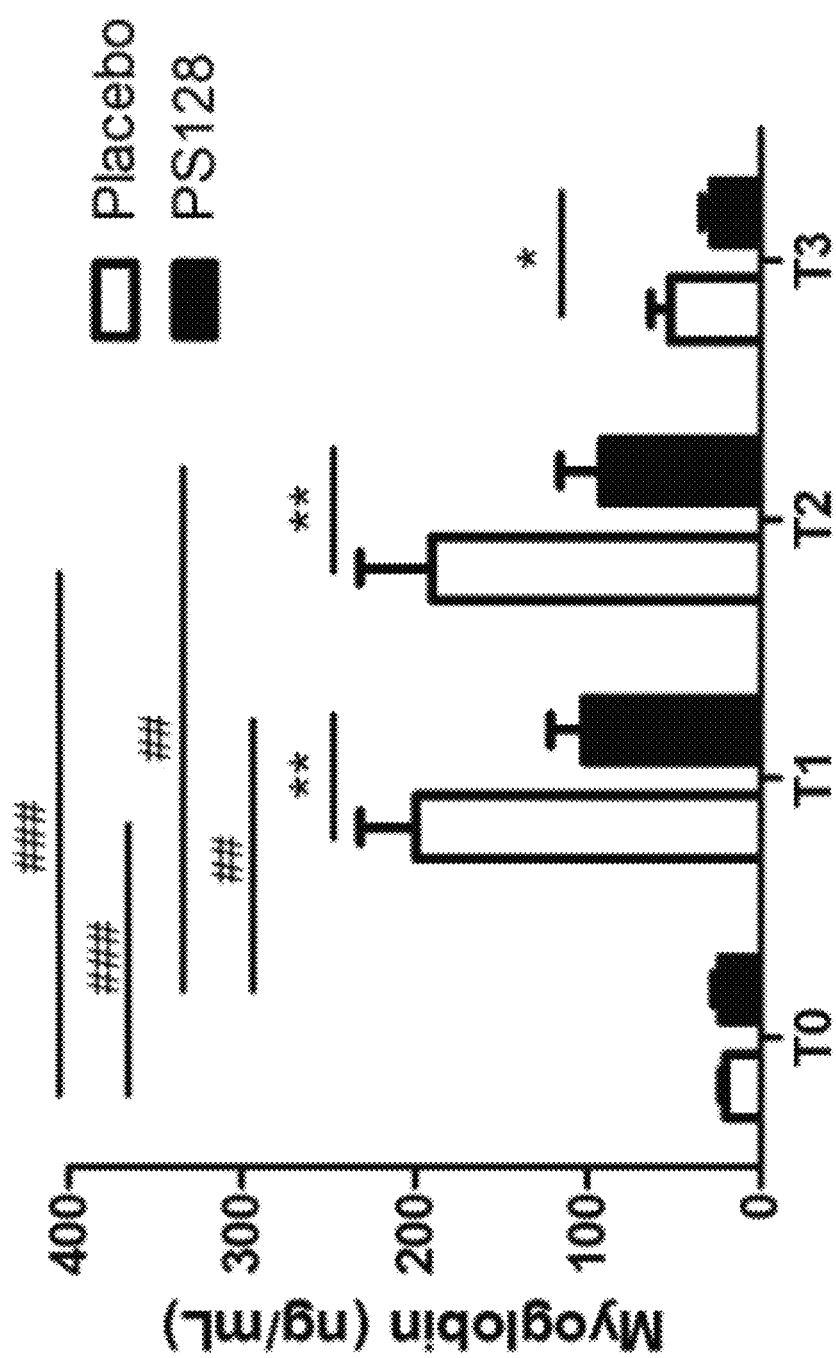
Figure 3C:
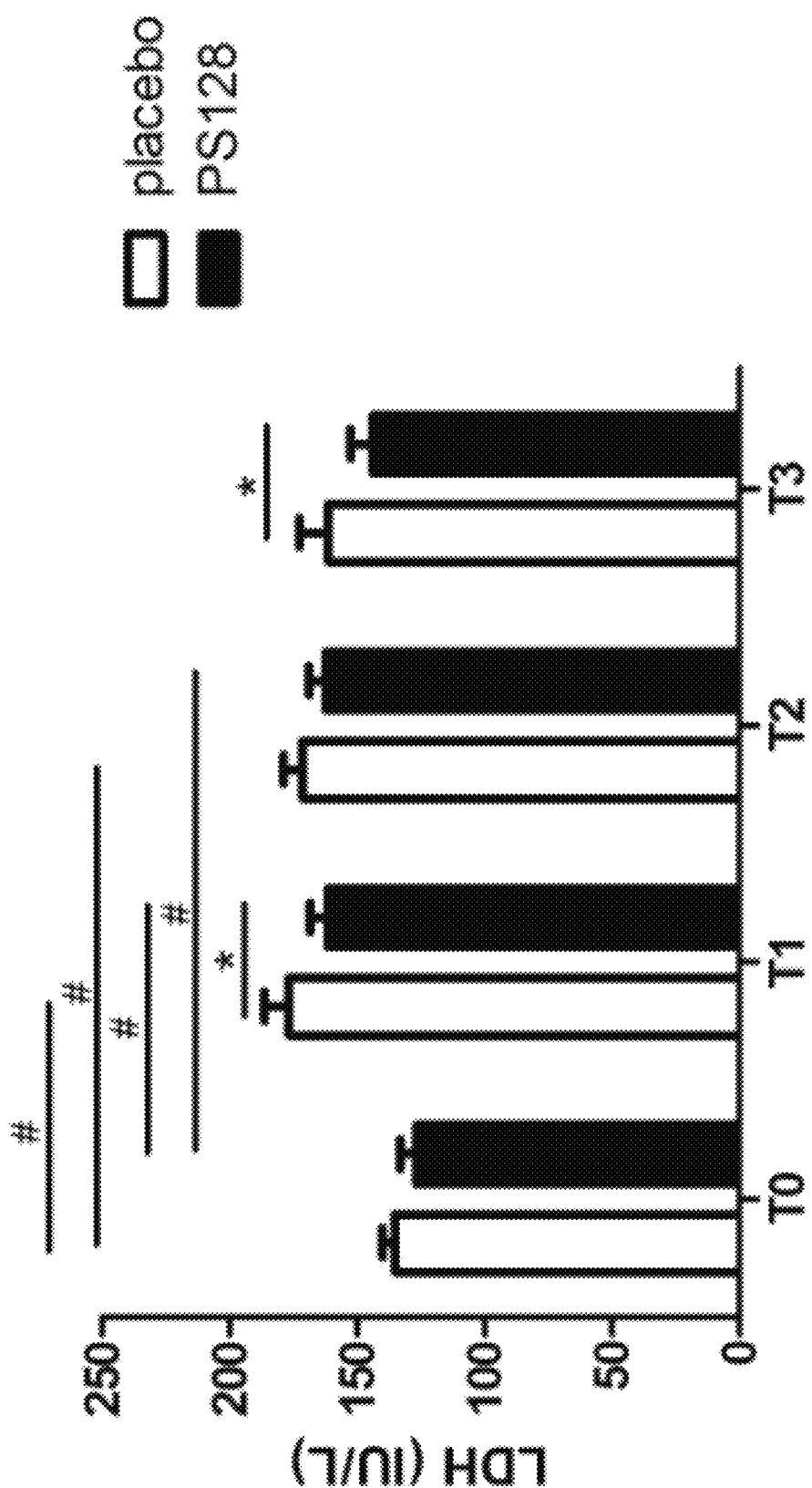
Figure 4A:
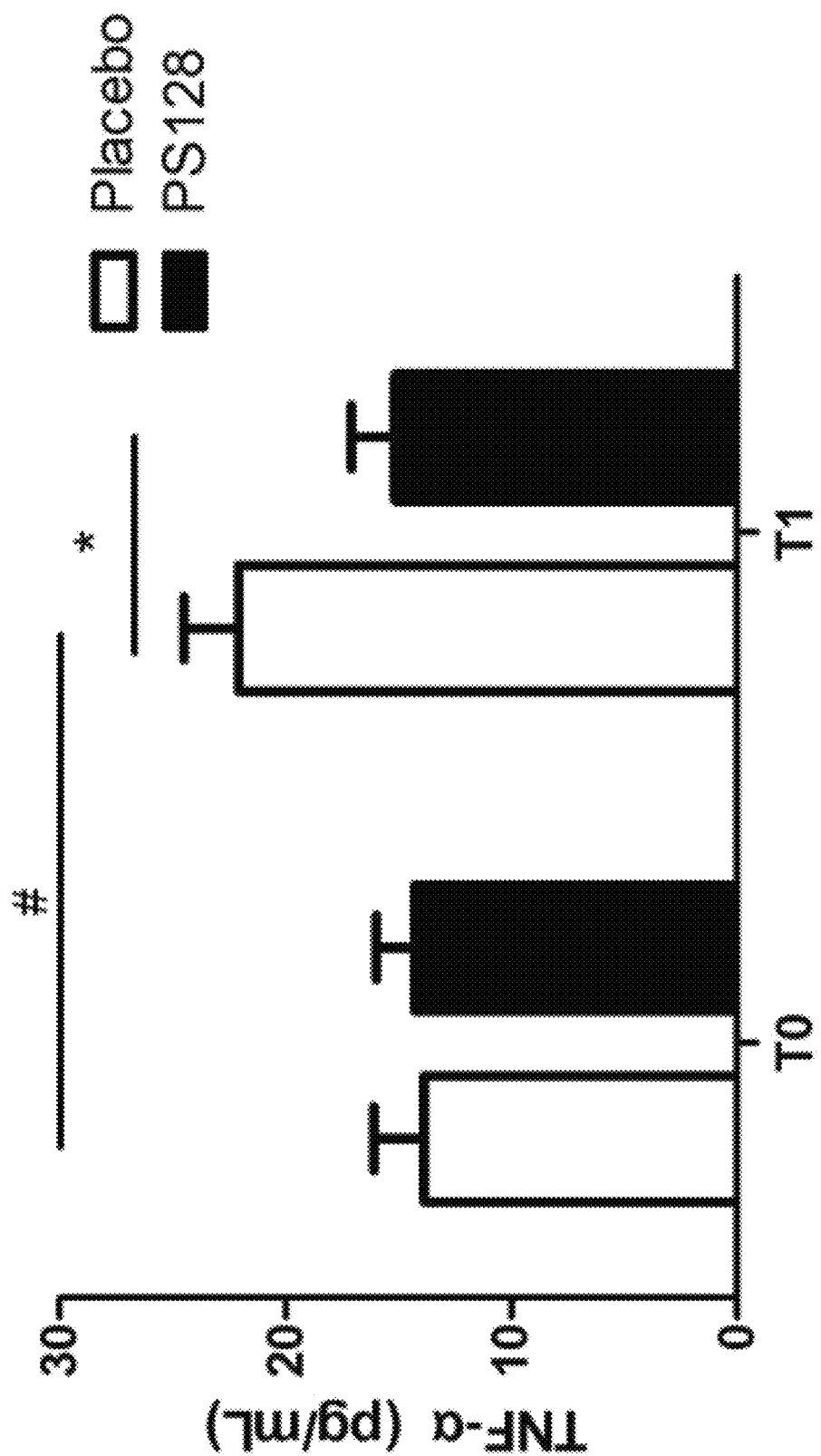
FIGS. 4A to 4D show the levels of the pro-inflammatory cytokines before and after the half marathon.
Figure 4B:
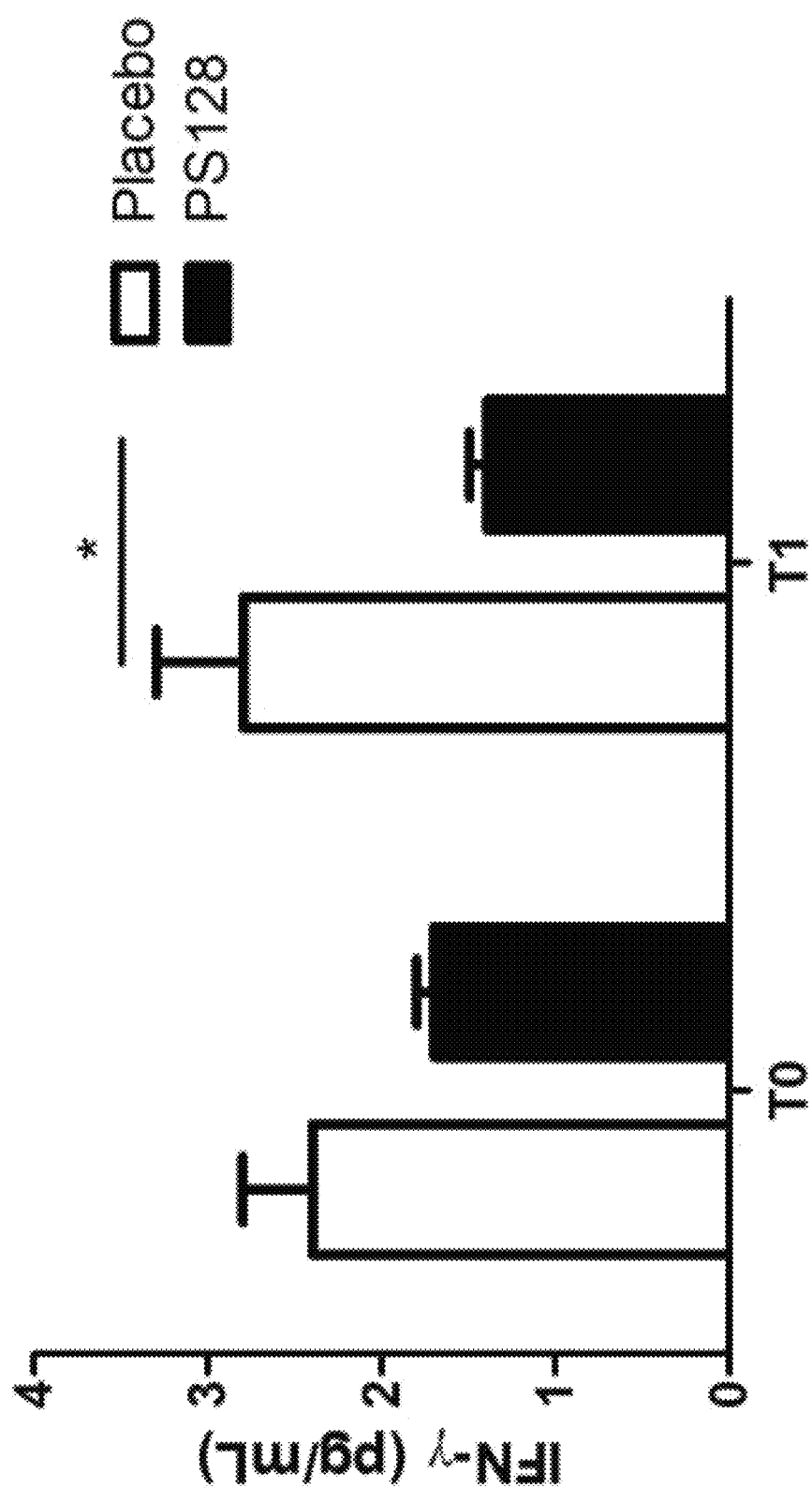
Figure 4C:
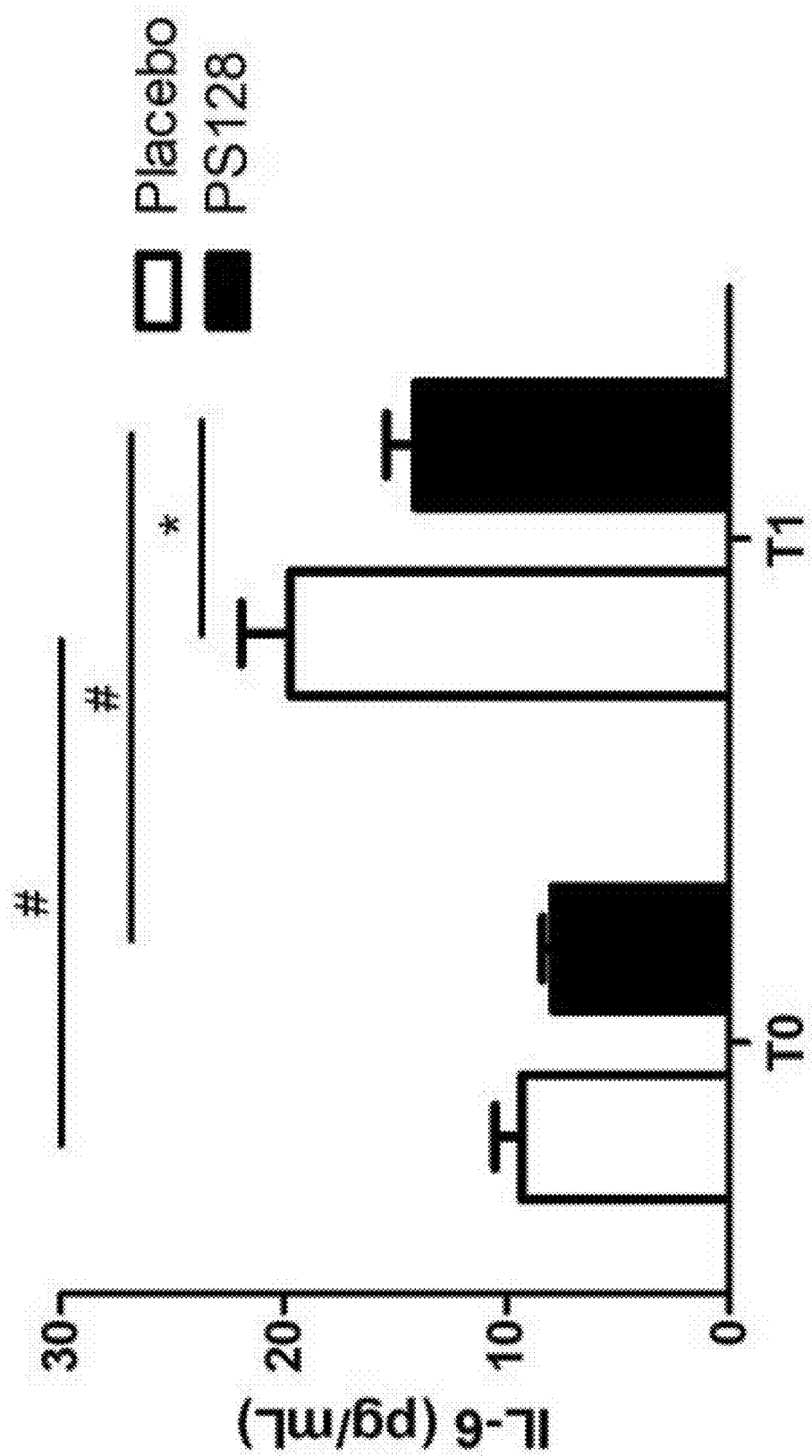
Figure 4D:
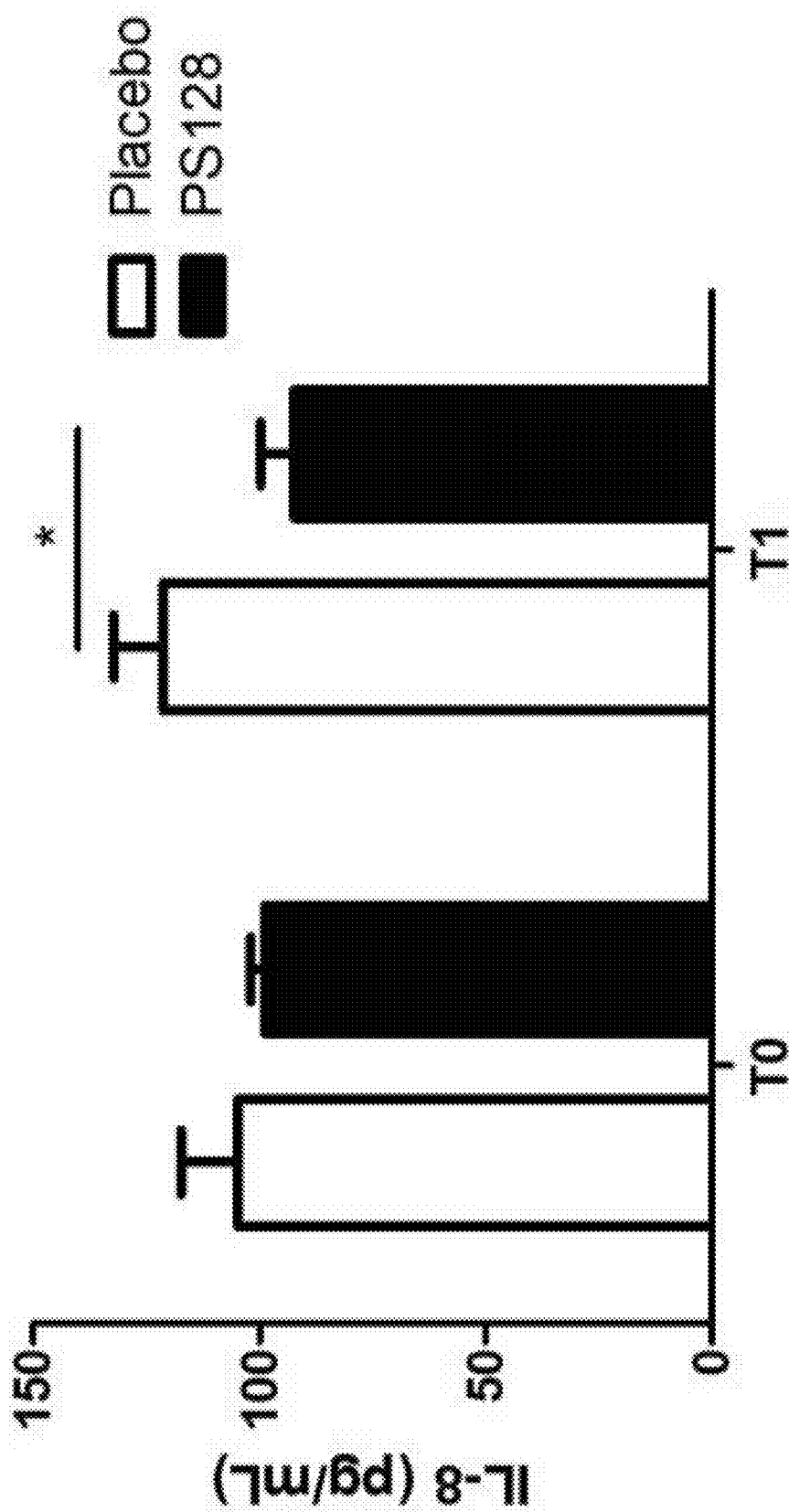

In addition, as shown in FIGS. 3A to 3C, creatine kinase (CK), myoglobin, and lactate dehydrogenase (LDH), which serve as the indicators for muscle damage, all showed significant decreases in the PS128 group, indicating that there is less muscle damage observed in the PS128 group.

Further, levels of inflammation markers such as tumor necrosis factor-α (TNF-α), IFN-γ (interferon-γ), IL-6, and IL-8 were observed to be significantly reduced in the PS128 group, when compared to the placebo group, indicating that PS128 has anti-inflammatory effects in the subjects receiving the PS128 supplements. As shown in FIGS. 4A to 4D, the levels of the pro-inflammation cytokines TNF-α (FIG. 4A), IFN-γ (FIG. 4B), IL-6 (FIG. 4C), and IL-8 (FIG. 4D) were significantly reduced in the PS128 group when compared to the placebo group immediately after exercise at the time point T1.

Figure 5A:
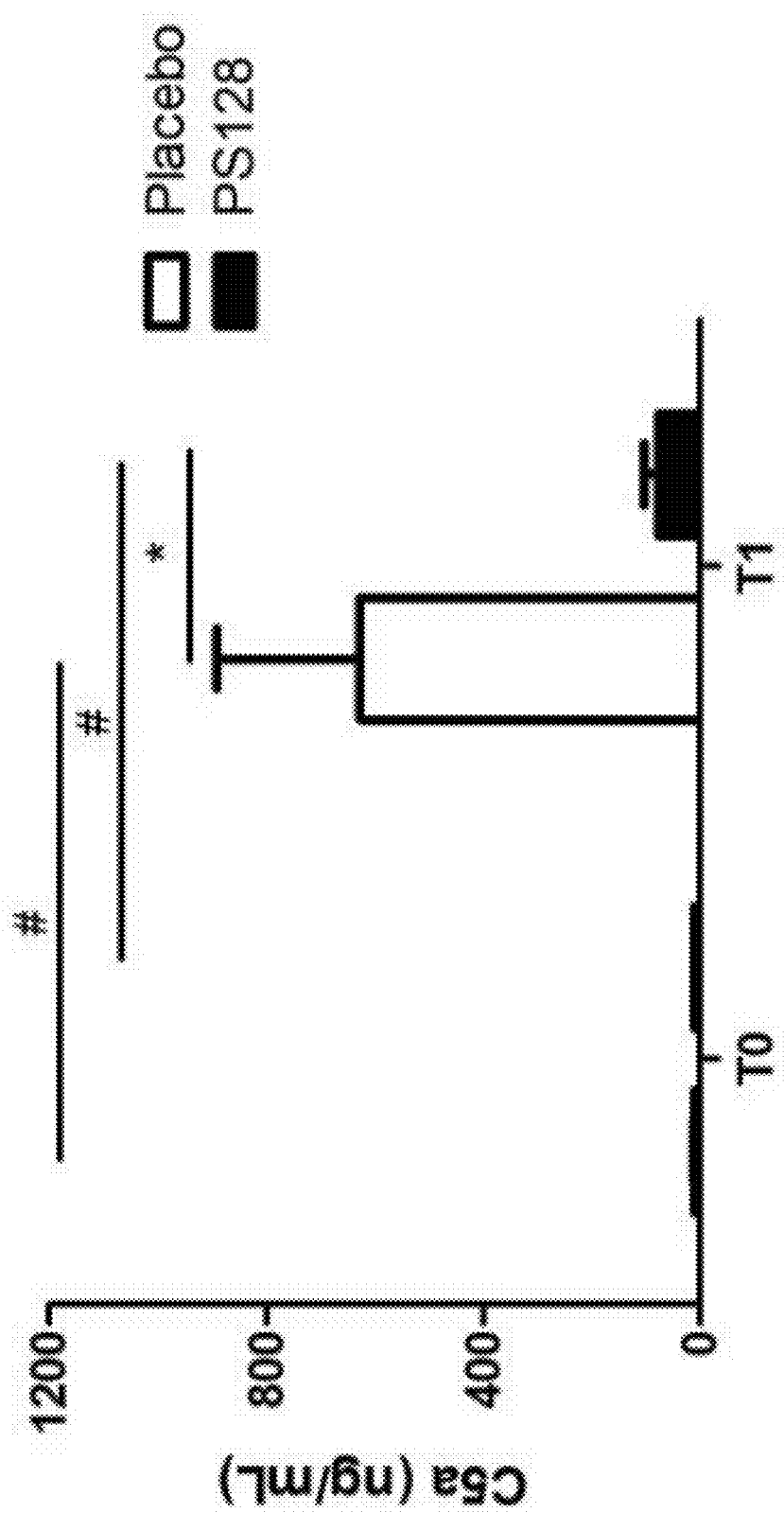
FIGS. 5A to 5D show the level of kidney injury and inflammation-associated markers before and after the half marathon.
Figure 5B:
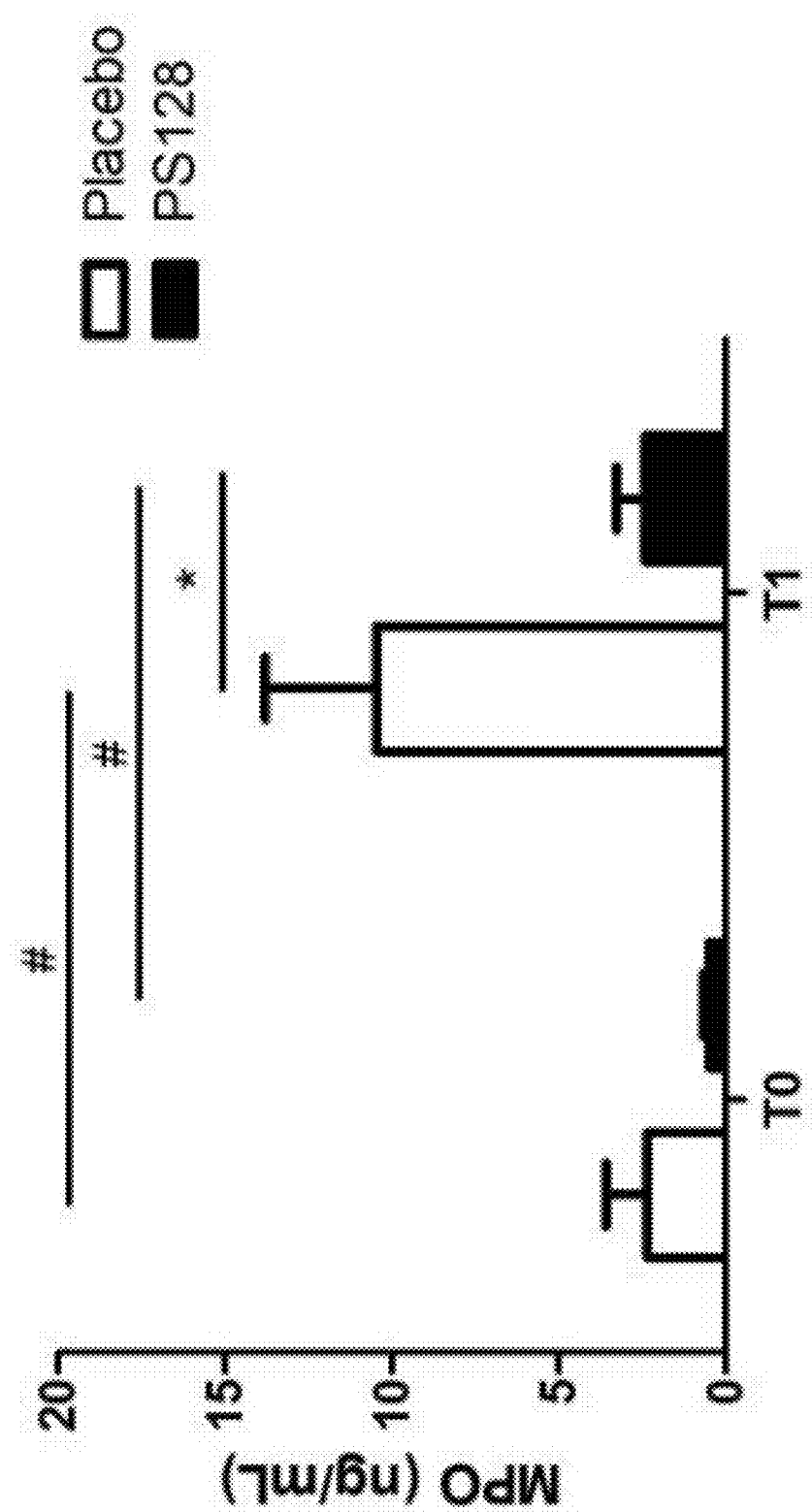
Figure 5C:
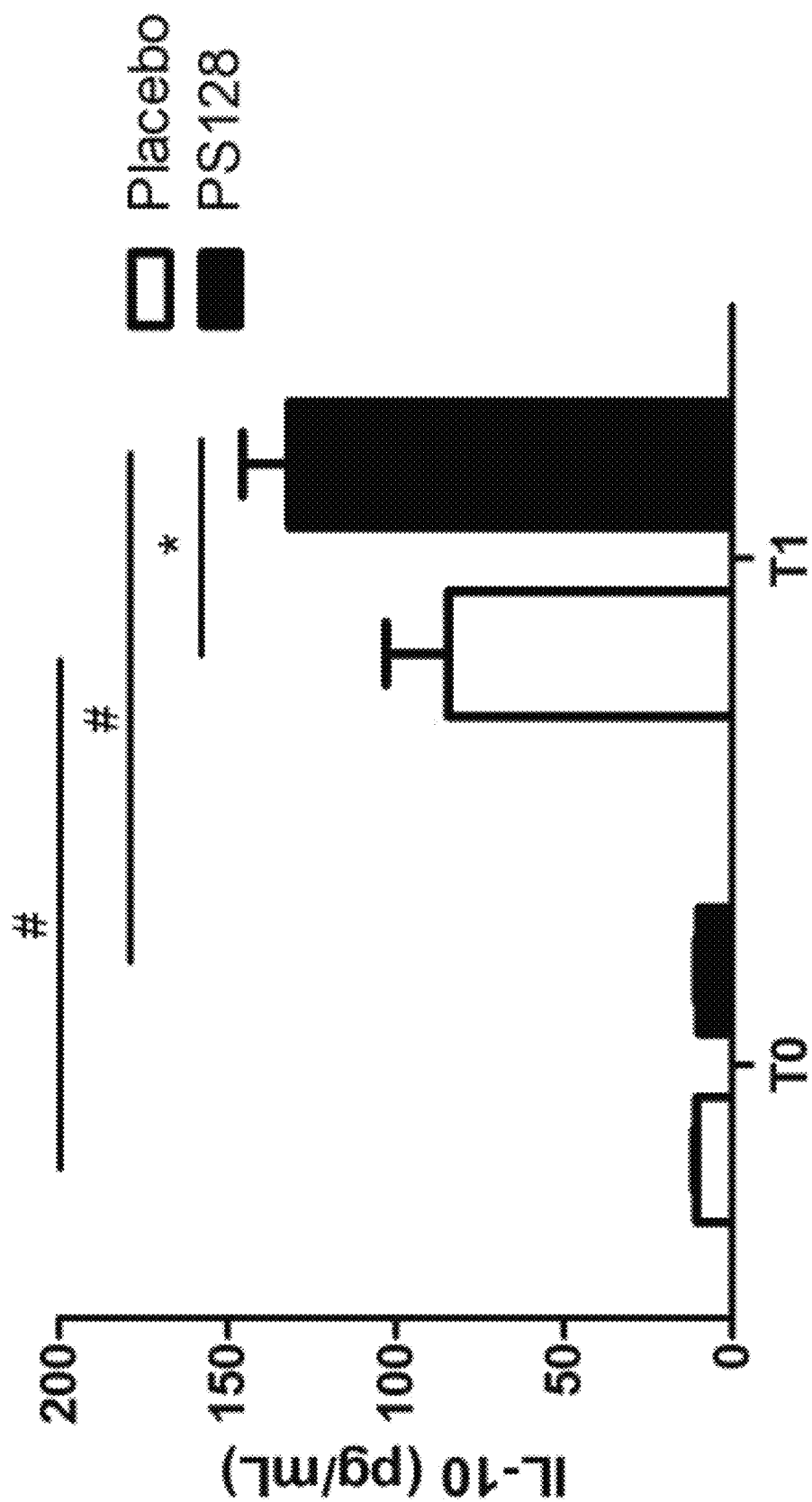
Figure 5D:
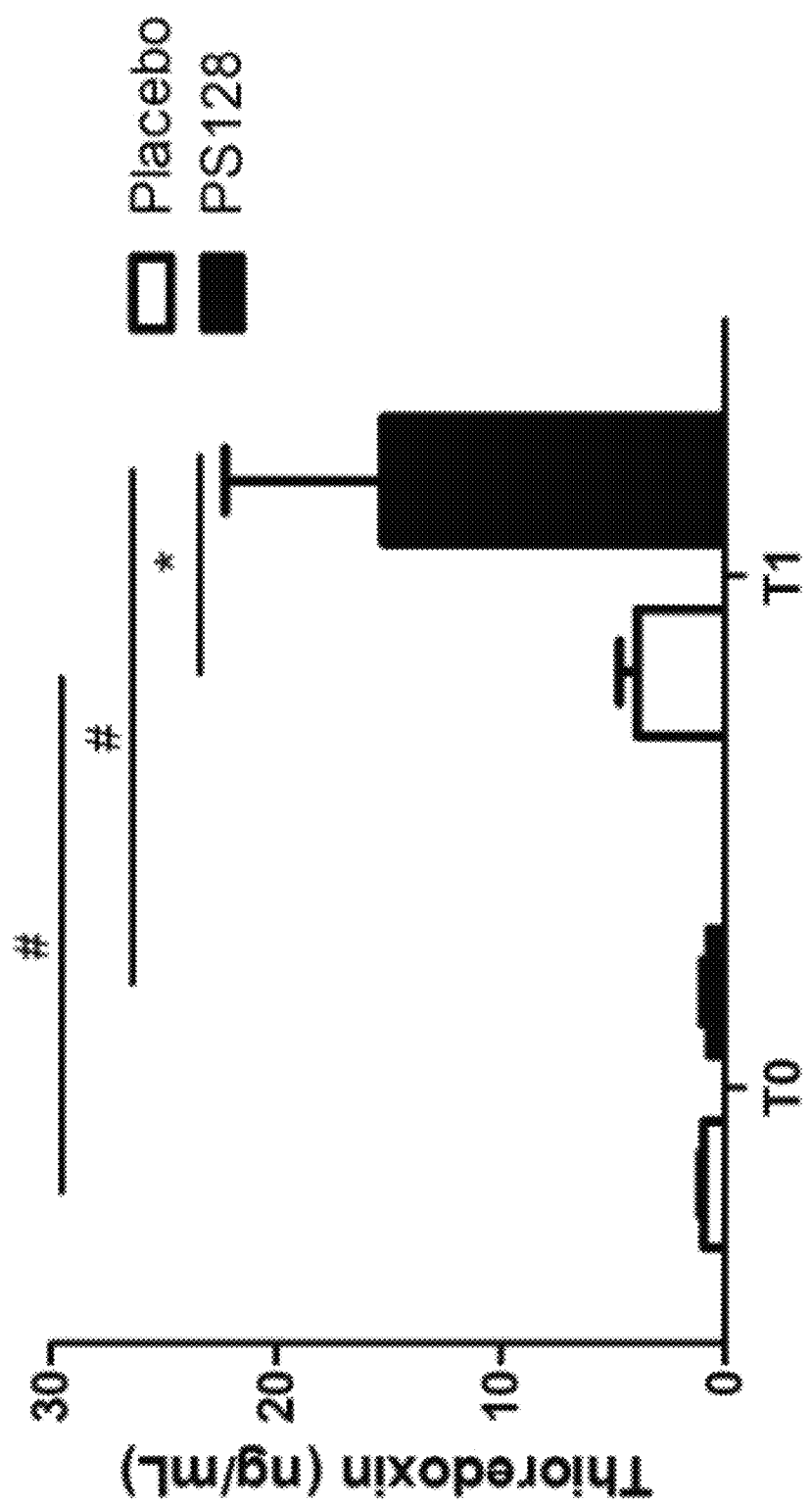

The levels of kidney injury and inflammation-associated markers such as C5a (FIG. 5A) and inflammation-associated markers such as myeloperoxidase (MPO) (FIG. 5B) in urine were observed to exhibit significantly lower levels in the PS128 group, while the serum anti-inflammation cytokine (IL-10) increased (FIG. 5C) and more thioredoxin (TRX) (FIG. 5D) was excreted and found in urine, with the PS128 supplements.

Figure 6:
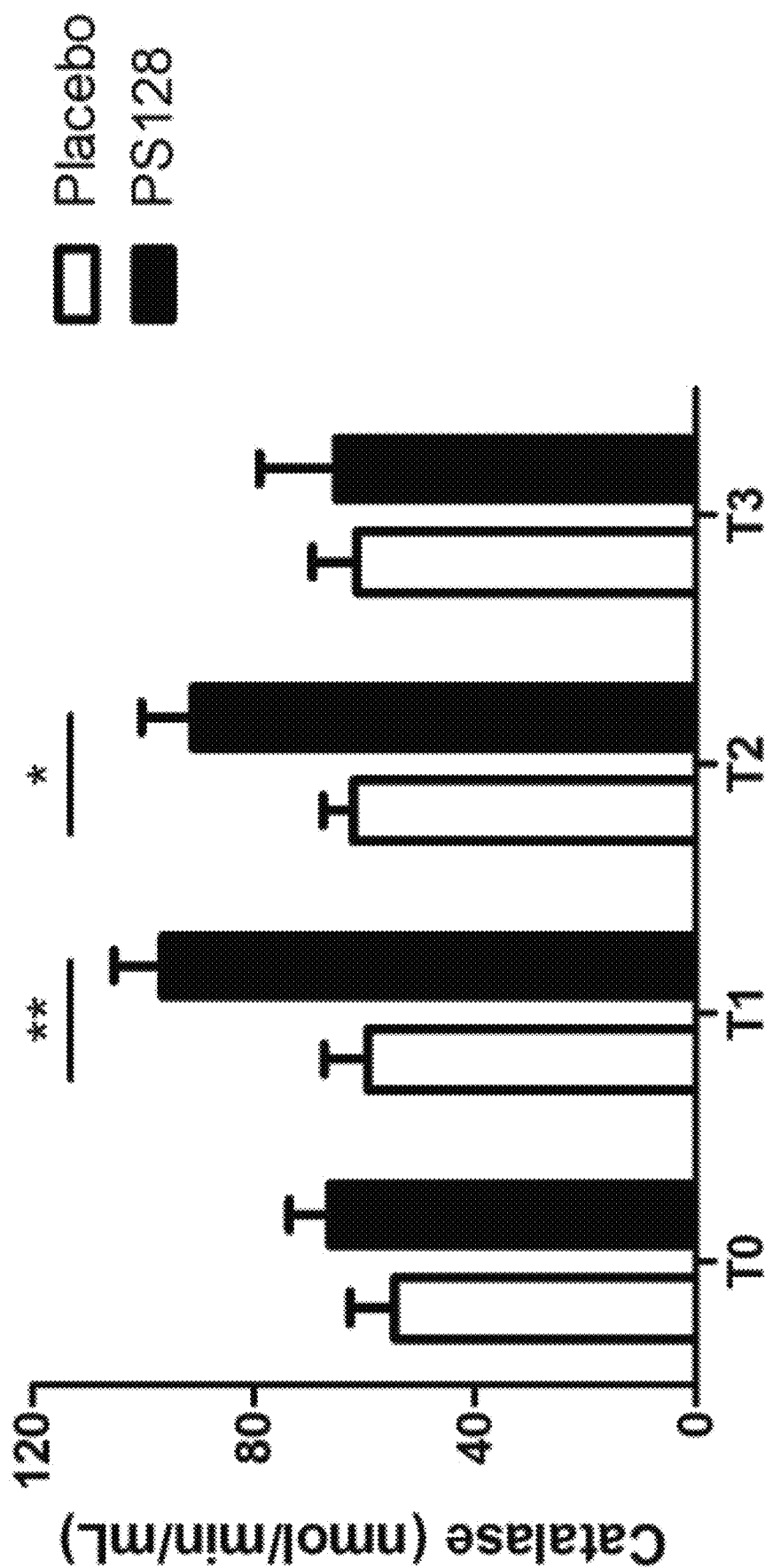
FIG. 6 shows the catalase level in the placebo and PS128 groups at different time points. The data are presented as mean±SEM. *$p<0.05$ and **$p<0.01$, comparison made between groups.

Also, the group of subjects receiving the PS128 supplements were shown to be protected from oxidation stress and had better renal function with the analysis of the catalase (CAT) level as shown in FIG. 6, where the CAT levels are significantly elevated in the PS128 group when compared to the placebo group at the same time point.

From the above, PS128 significantly modulated TRX and MPO levels by elevating anti-oxidative capacities. On the other hand, the pro-inflammatory mediator C5a may also be significantly regulated by PS128-mediated IL-10 production. Therefore, PS128 not only decreased inflammatory cytokines but also elevated the production of anti-inflammatory cytokines. Hence, PS128 has the effect on inflammation or oxidation modulation. Furthermore, PS128 also demonstrated a significant elevation of BCAAs content in the plasma samples.

It was also noted that the CK was significantly lower in the PS128 group at different time points after exercise. At the extended time points after exercise, PS128 maintained the beneficial effects on lowering the levels of inflammatory cytokines.

That is, PS128 has the sustained effect on the lowering of the inflammatory cytokine levels, thereby protecting muscles from damage.

Example 2: Enhanced Physical Performance and Recovery in Subjects Receiving PS128 Supplements Subjects in both the PS128 group and the placebo group were evaluated for their anaerobic and aerobic capacities with Wingate protocol and with Bruce protocol, respectively. Details of the protocols are well known by a skilled person in the art. For example, subjects in both groups were tested for $VO_2$ max with the Bruce protocol for aerobic power, and anaerobic power with the Wingate protocol at 24 h before exercise, 24 h after exercise, and 96 h after exercise. Additional tests for anaerobic power with the Wingate protocol were carried out at 3 h, 48 h and 72 h after exercise.

For the Wingate protocol, the subjects were required to try their best on the bike for 30 seconds with timely encouragement after the end of the warm-up stage. During the 30-second test period for the Wingate anaerobic kinetic test on a stationary bicycle, the bike recorded and analyzed the subjects' number of laps, watts produced, peak anaerobic power (PAP), mean power (MEP), and fatigue index (FAO, which were all described in prior art and well known to a person skilled in the art.

Figure 7A:
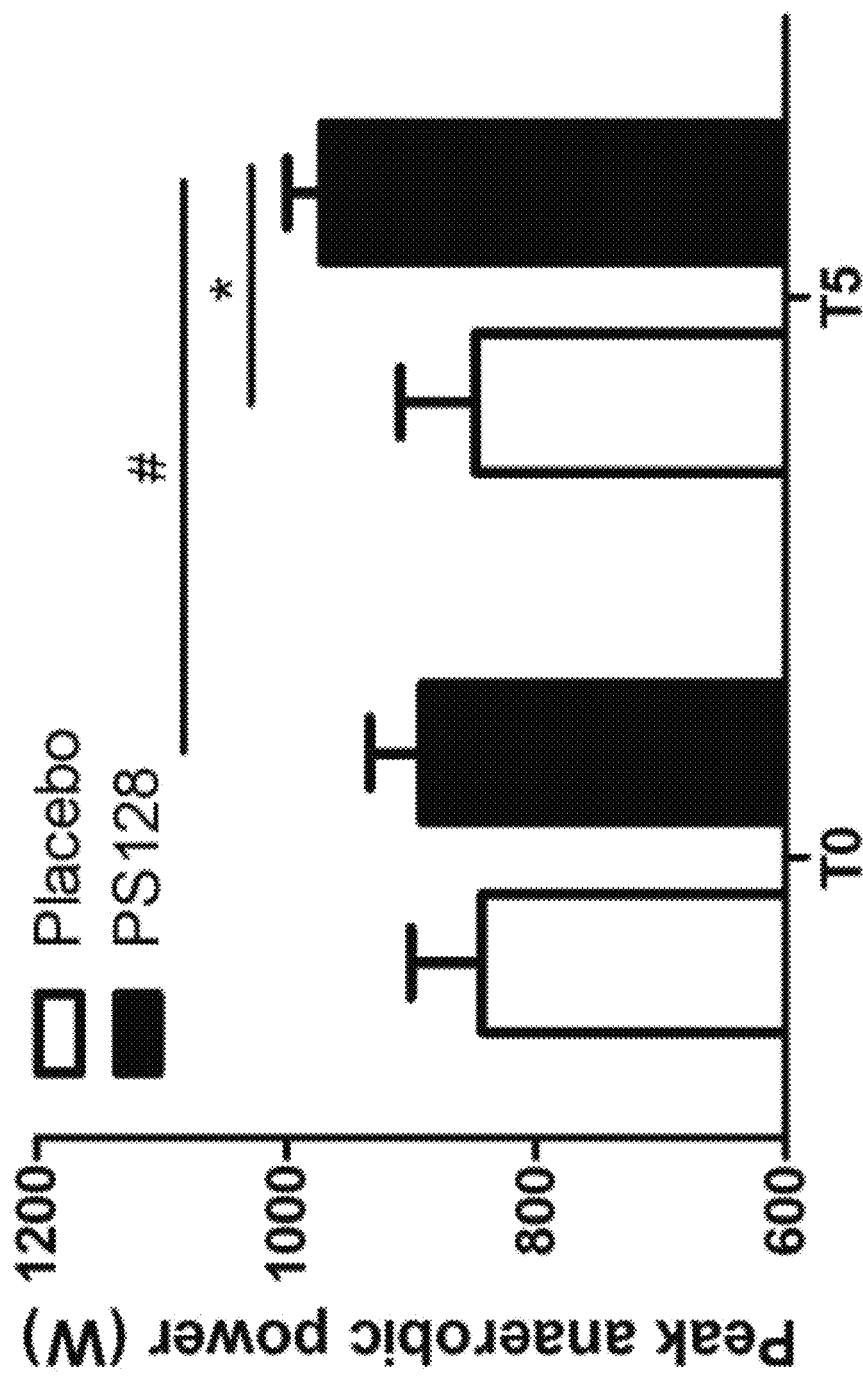
FIGS. 7A to 7D show the anaerobic and aerobic exercise capacities before and after the half marathon.
Figure 7B:
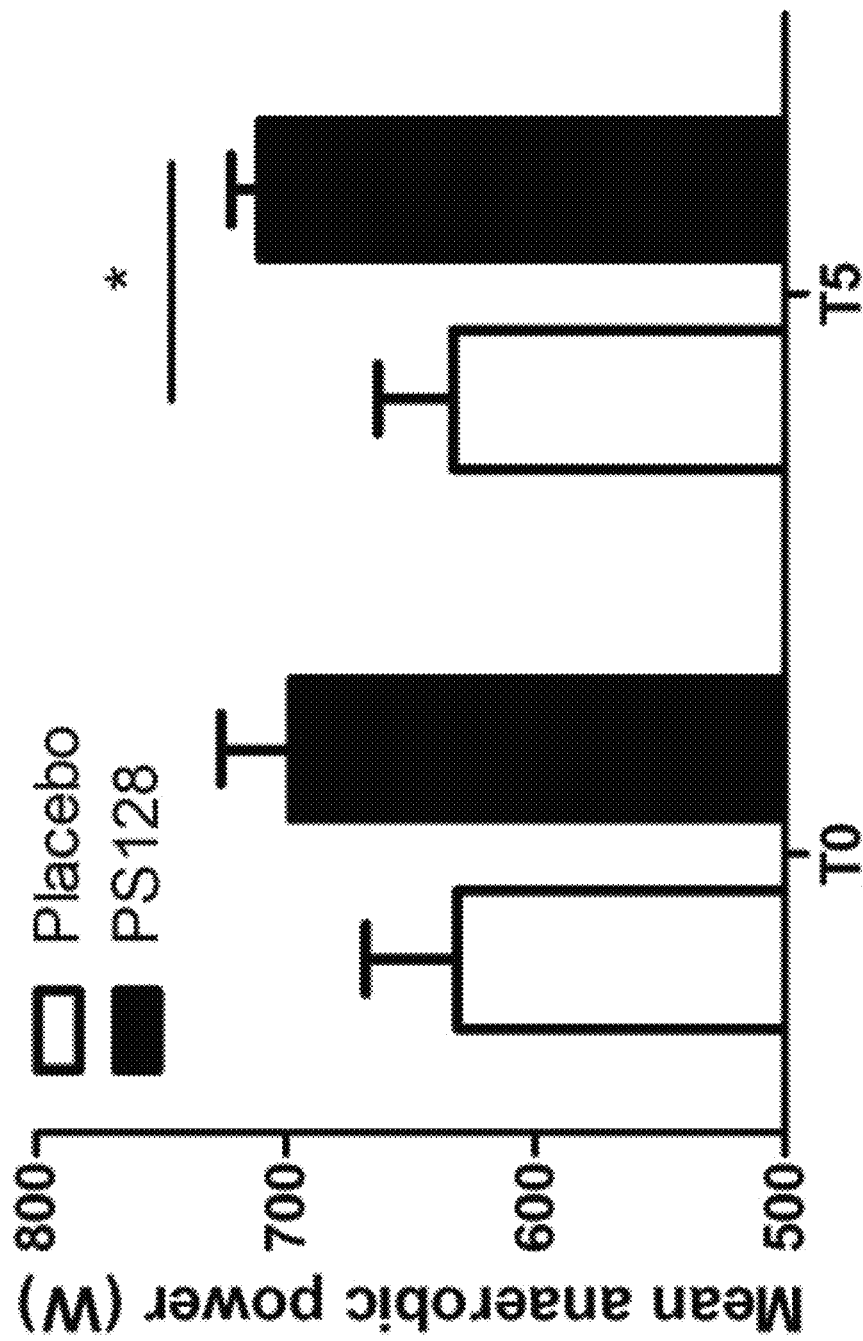
Figure 7C:
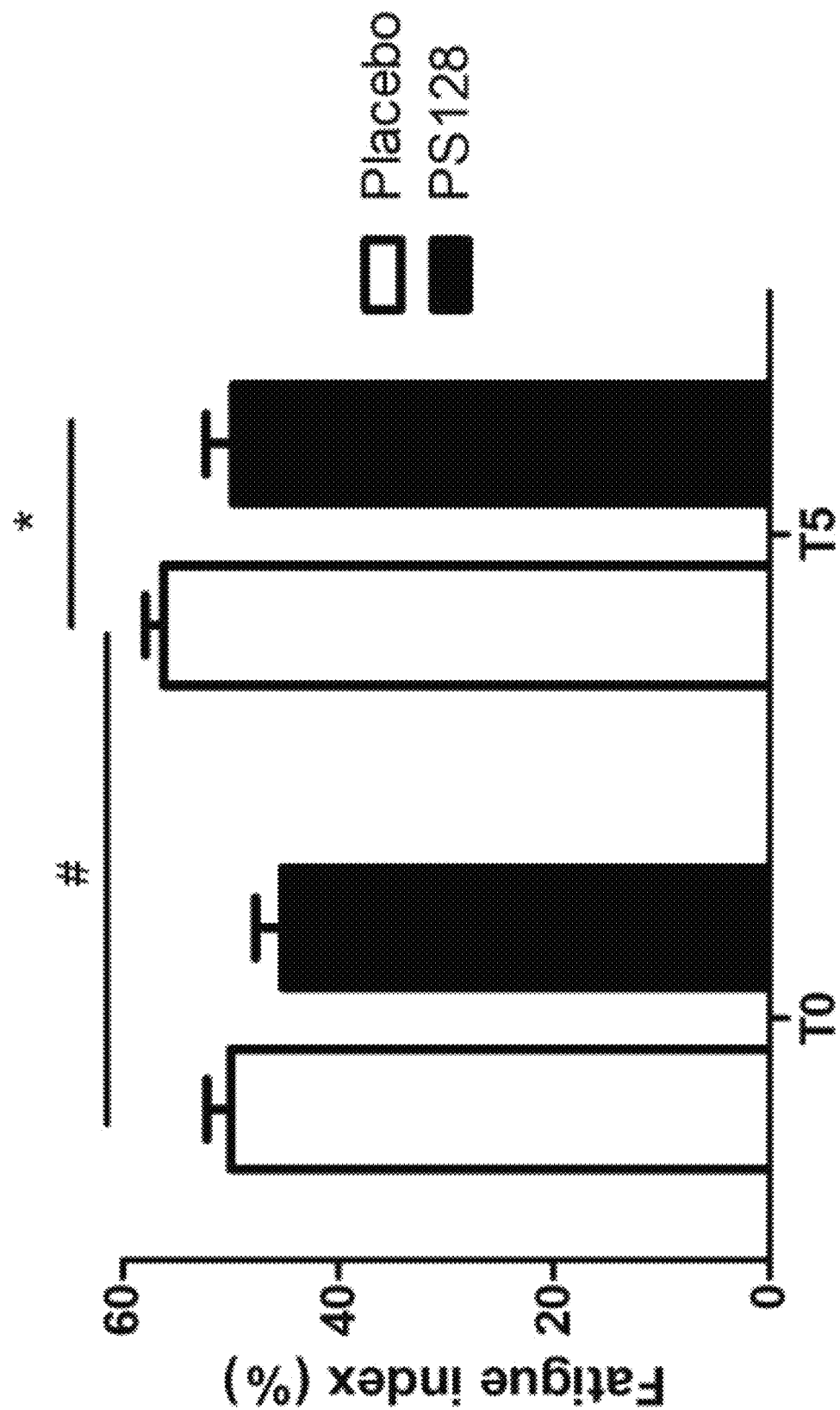

The results showed that the PS128 group has increased PAP (FIG. 7A) and MEP (FIG. 7B) and decreased FAI (FIG. 7C), and thus has better physical performance and recovery rate as compared with the placebo group.

Figure 7D:
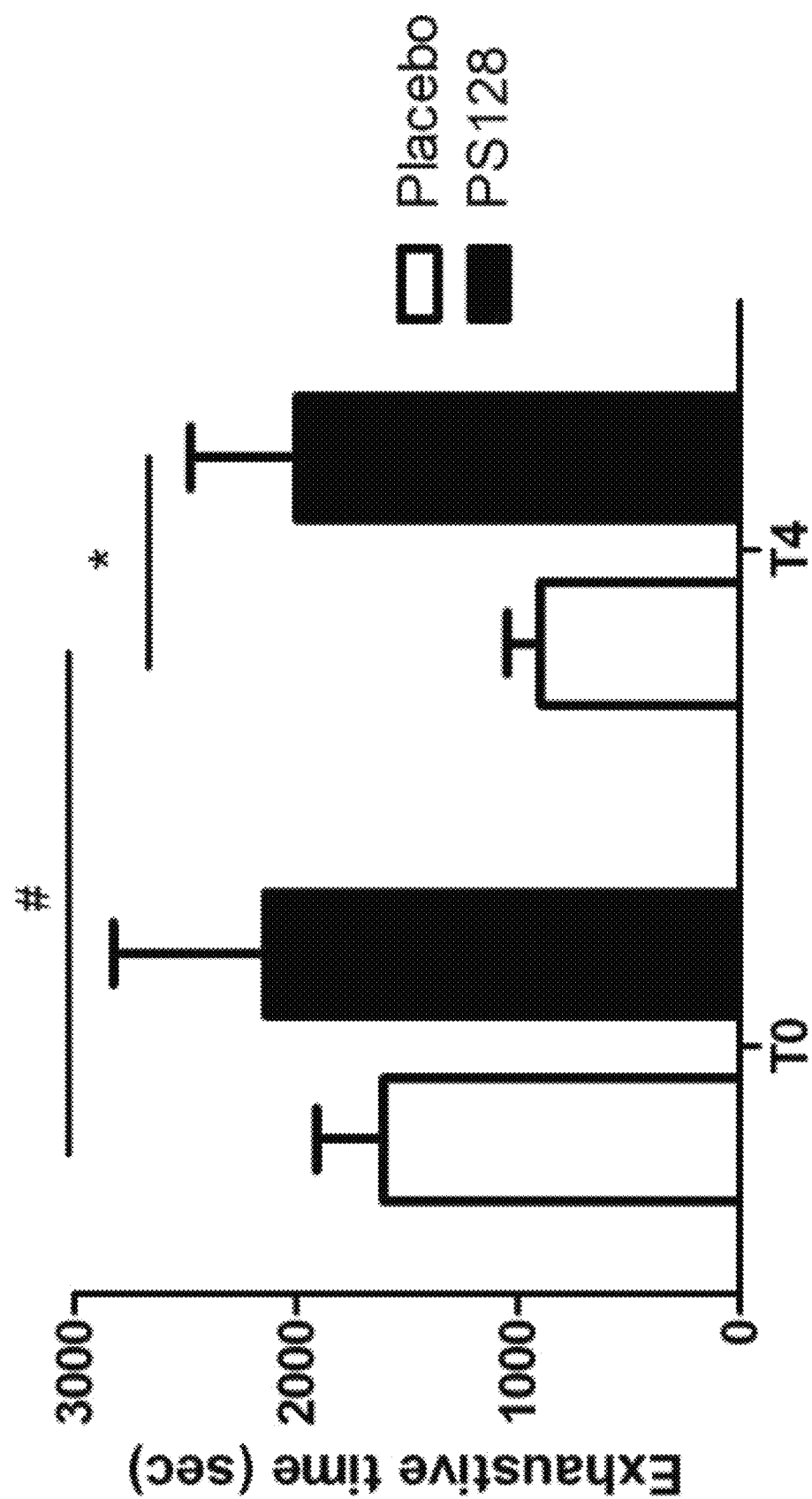

For the Bruce protocol, the $VO_2$ max endurance test was performed on a Cortex gas analyzer and a stationary bicycle. Subjects were given a fixed period of time to warm-up and also time for rest before taking the test. The 85% $VO_2$ max speed, which was adjusted by individual $VO_2$ max, was applied to an individual subject until exhaustion for endurance assessment. As shown in FIG. 7D, the exhaustive time in the PS128 group is significantly longer than the placebo group, both before and after exercise, indicating that administration of PS128 improves the physical endurance of the subjects. PS128 thus provides the subjects with better physical performance.

Electromyography (EMG) activity of the quadriceps and hamstring of the subjects were also recorded at all seven time points, that is, T0 to T6 as described above. For example, the median frequency (MF) and maximal voluntary isometric contraction (MVIC) of the hamstrings and quadriceps were recorded in both groups to evaluate the physical performance. MF values obtained by EMG have been used to understand the recruitment characteristics of quadriceps and hamstrings in the studies. To do so, EMG normalization is frequently used to improve reliability by decreasing variation within and between individuals in EMG studies, and maximal voluntary isometric contraction (MVIC) is a common method of normalization used as the standard reference for comparison between subjects, days, studies and muscles. The results showed that PS128 benefits the MVIC and EMG performance and facilitates muscle strength recovery.

Figure 8A:
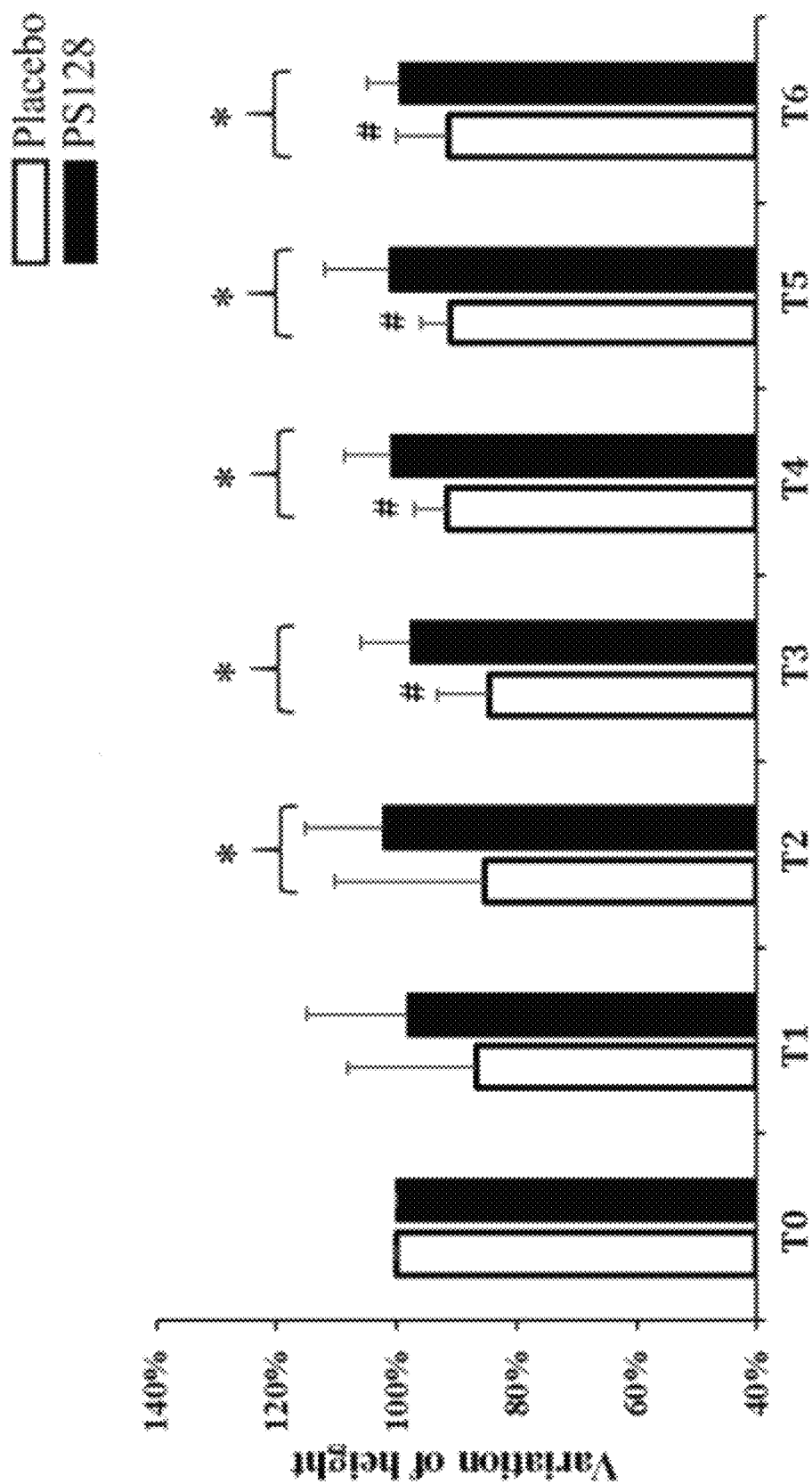
FIGS. 8A and 8B show the power of lower extremity at different time points.
Figure 8B:
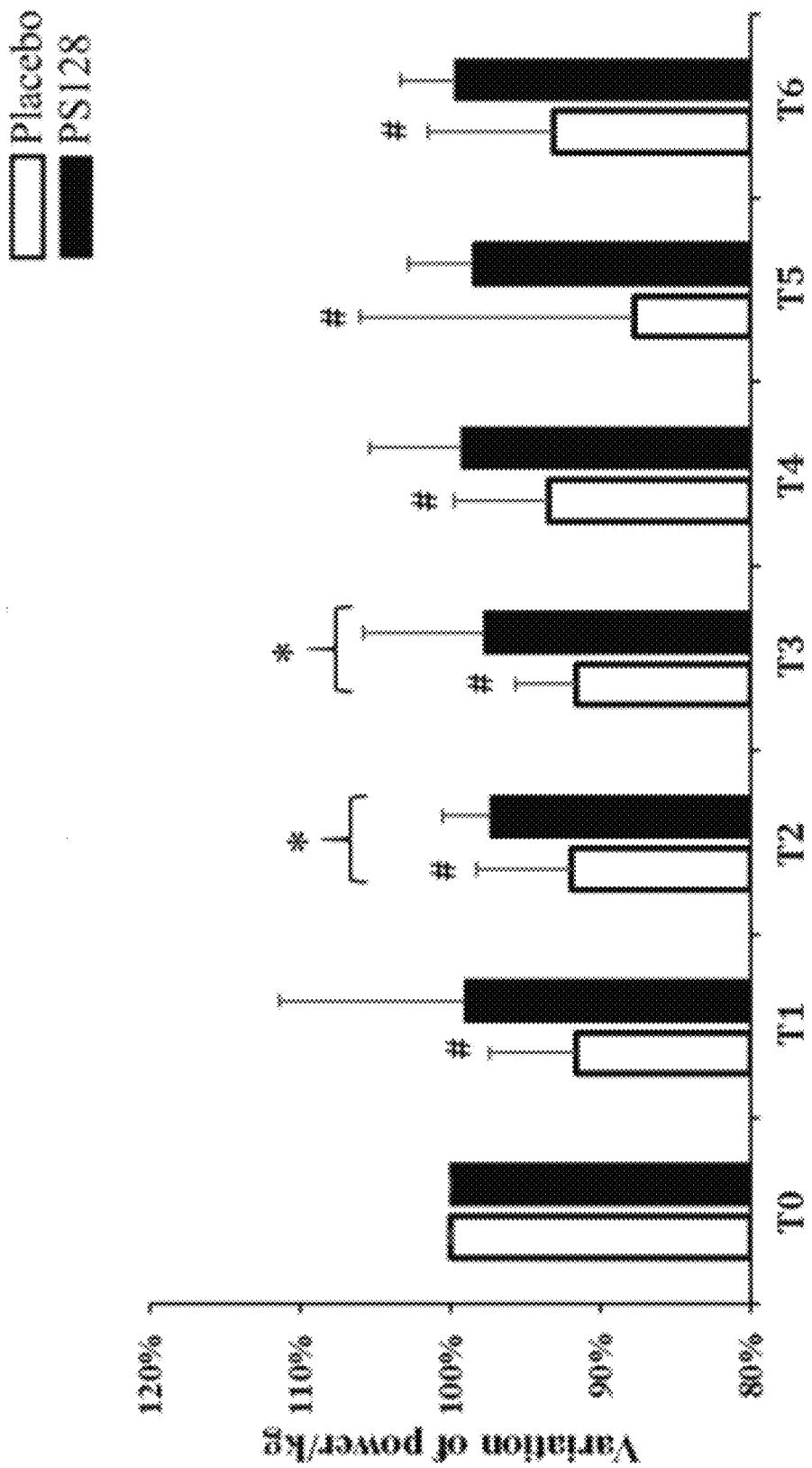

As shown in FIGS. 8A and 8B, the PS128 group is shown to enhance the physical performance in the subjects receiving PS128 supplements. For example, the subjects were also asked to do countermovement jump to evaluate their physical strength and capacity at all seven time points as described above. Again, the PS128 group was shown to enhance the muscle strength in the subjects receiving PS128 supplements compared to the subjects receiving only placebo, with higher countermovement jump height (FIG. 8A) and greater countermovement jump power (FIG. 8B).

Also, the body composition of the subjects measured by using a dual energy X-ray absorption (DEXA) was evaluated before and after the exercise (half marathon). After X-rays of different energies penetrate the bone and soft tissues, the X-ray absorption or attenuation of different tissues was calculated by the built-in formula of the absorptiometer. Again, the PS128 group was shown to enhance the muscle mass in the subjects receiving the PS128 supplements.

Figure 9A:
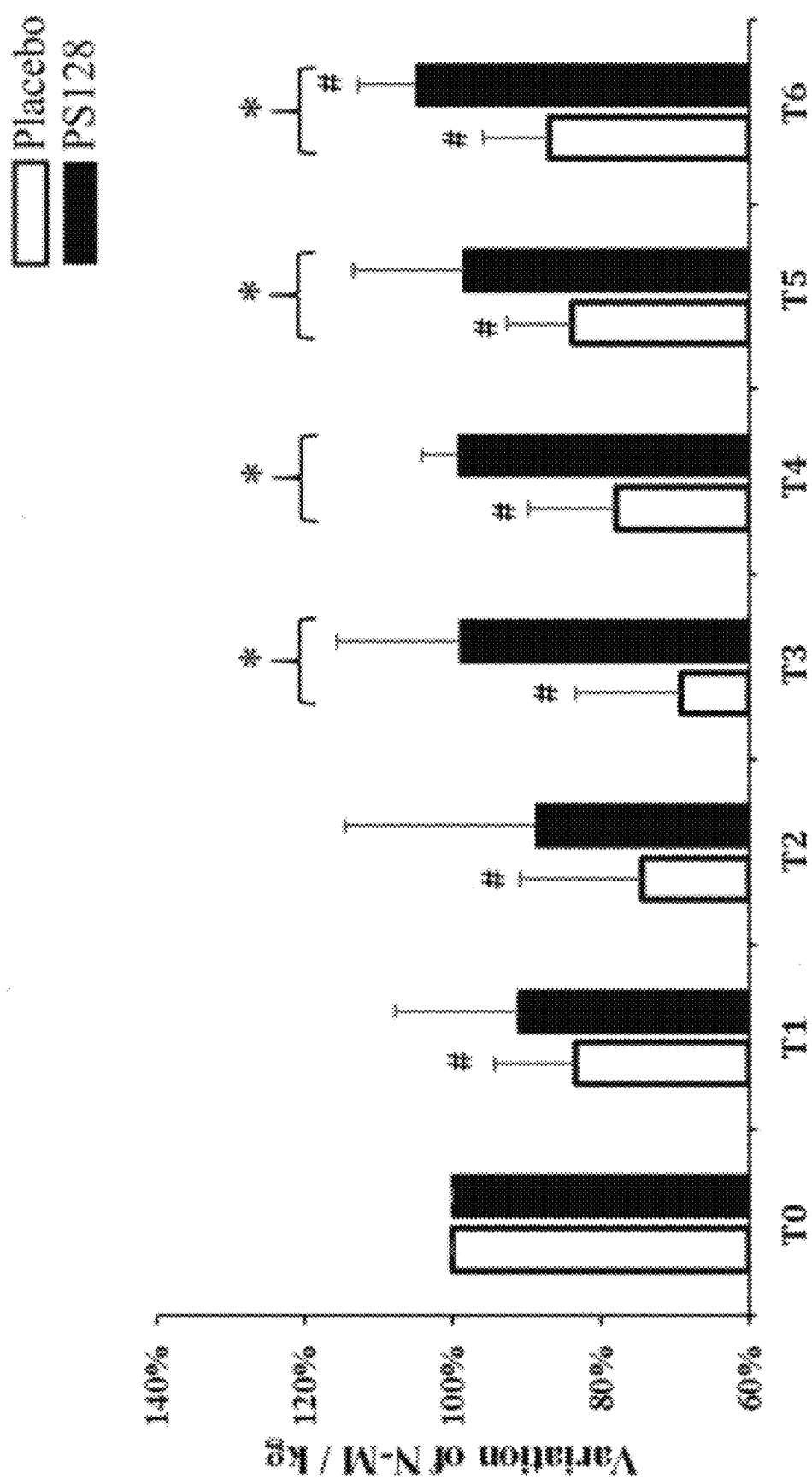
FIGS. 9A to 9D show the strength of lower extremity at different time points.
Figure 9B:
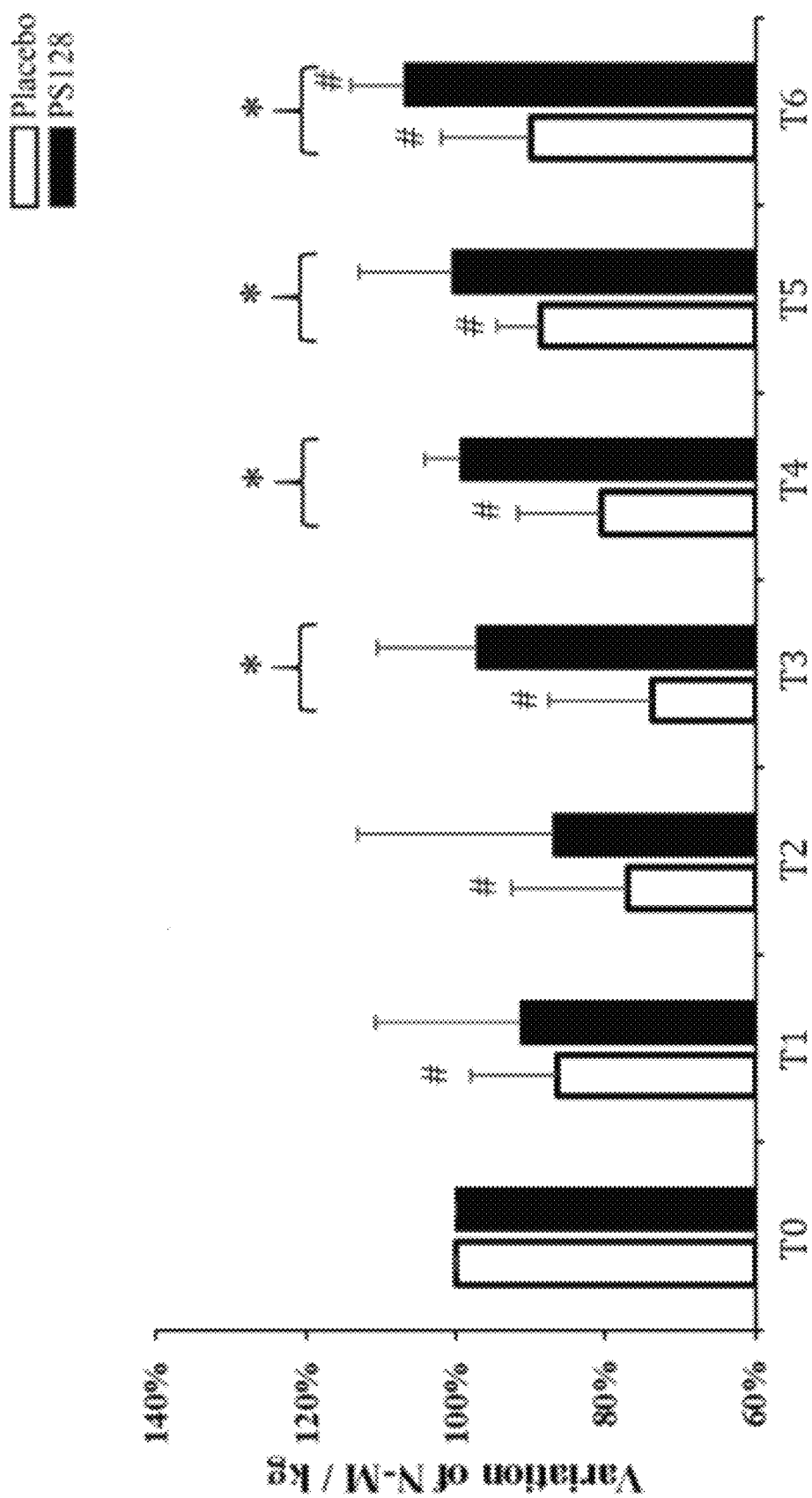
Figure 9C:
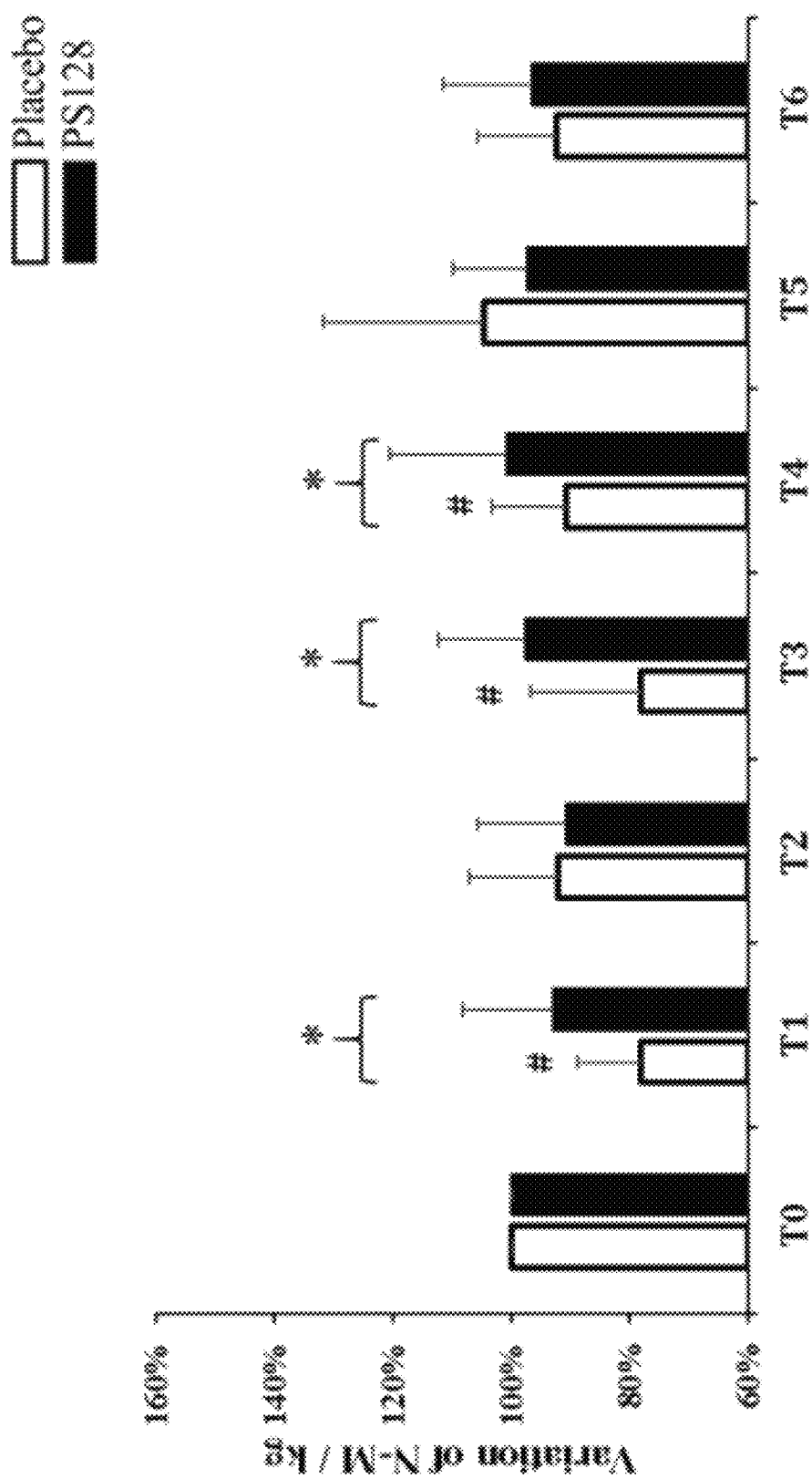
Figure 9D:
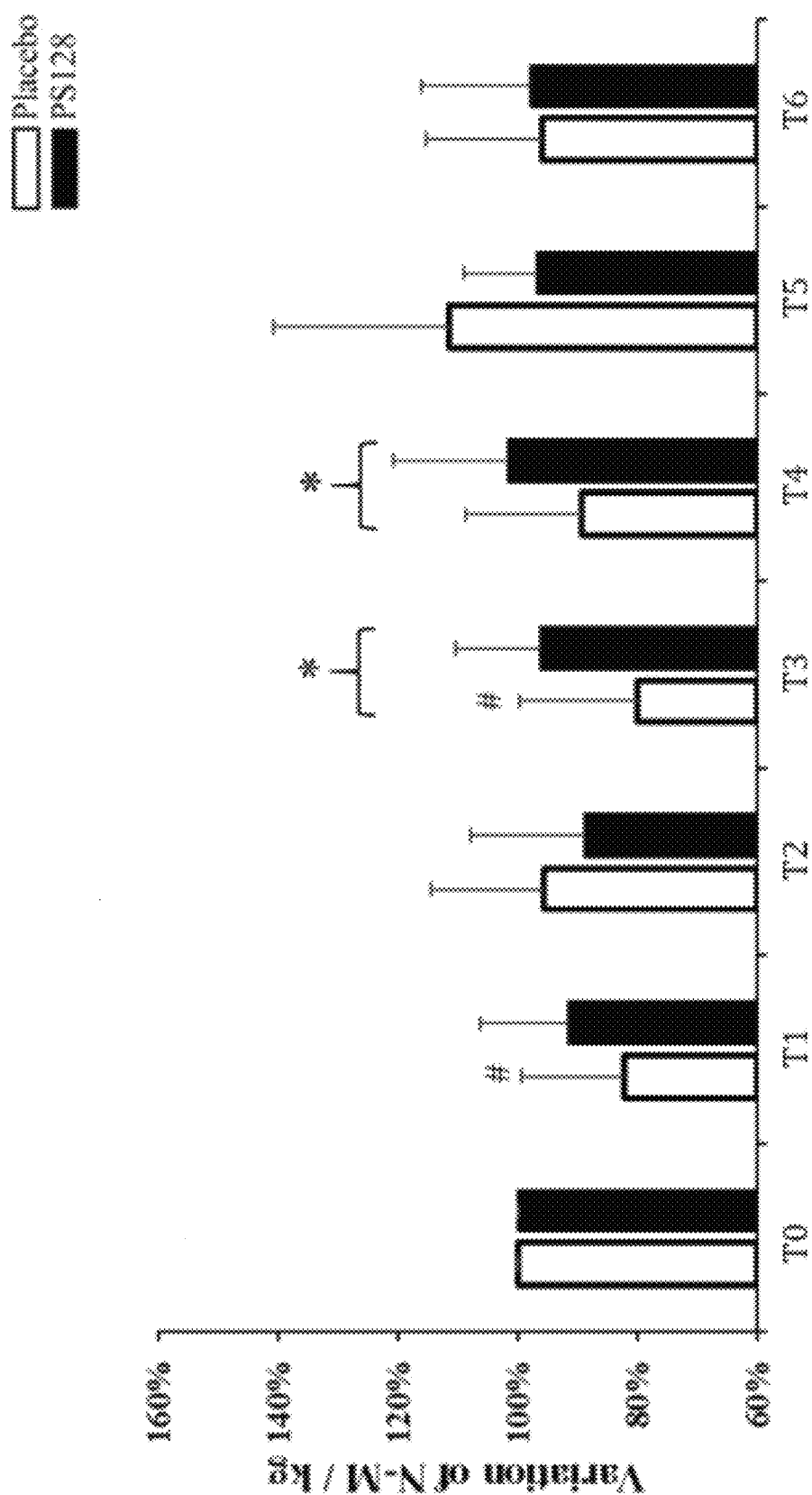

The physical performance is further evaluated by measuring the strength of lower extremity in the PS128 and placebo groups at different time points, as shown in FIGS. 9A to 9D. The knee extensor peak torque (FIG. 9A) and knee extensor average torque (FIG. 9B) showed significantly higher values in the PS128 group than those in the placebo group. FIGS. 9C and 9D showed that knee flexor peak torque and knee flexor average torque are significantly higher in the PS128 group than those in the placebo group at several time points after exercise.

The subjects' anaerobic and aerobic exercise capacities may be compensated for by exercise-induced fatigue, or the subjects could have maintained their performance. Therefore, PS128 may be a potential ergogenic aid to improve the health of subjects by reducing the exercise-induced fatigue and increase their physical performance.

It was found that the subjects in the PS128 group have better exercise capacities, endurance and recovery as shown by the PAP, MEP, and FAI values. It was further noted that PS128 could maintain MEP and FAI after exercise compared to pre-exercise data. These findings may confer potential benefits in the field of sports science in that PS128 could exert the beneficial effects on exercise performance maintenance and recovery. Therefore, PS128 could be considered as an alternative option for nutritional supplementation not only for performance but also for physiological adaption.

While some of the embodiments of the present disclosure have been described in detail in the above, it is, however, possible for those of ordinary skill in the art to make various modifications and changes to the embodiments shown without substantially departing from the teaching and advantages of the disclosure. Such modifications and changes are encompassed in the spirit and scope of the disclosure as set forth in the appended claims.

What is claimed is:

1. A method of reducing exercise fatigue in a subject, comprising administering a composition comprising an effective amount of *Lactobacillus plantarum* subsp. *plantarum* PS128 and a carrier thereof to the subject in need thereof.

2. The method of claim 1, further comprising preventing muscle damage in the subject.

3. The method of claim 1, further comprising reducing inflammation in the subject.

4. The method of claim 1, further comprising reducing kidney injury in the subject.

5. The method of claim 1, further comprising increasing physical strength of the subject.

6. The method of claim 1, further comprising increasing physical capacity of the subject.

7. The method of claim 1, further comprising increasing endurance of the subject.

8. The method of claim 1, further comprising reducing muscle fatigue in the subject.

9. The method of claim 1, further comprising reducing oxidation stress in the subject.

10. The method of claim 1, further comprising enhancing physical performance of the subject.

11. The method of claim 1, further comprising facilitating muscle strength recovery of the subject.

12. The method of claim 1, wherein the *Lactobacillus plantarum* subsp. *plantarum* PS128 is administered to the subject at an amount of at least $10^9$ CFU per day.

13. The method of claim 1, wherein the composition is a nutritional composition or a pharmaceutical composition.

14. The method of claim 1, wherein the composition is prepared for oral administration.

* * * * *